US012559516B2

(12) United States Patent
Kataoka et al.

(10) Patent No.: US 12,559,516 B2
(45) Date of Patent: Feb. 24, 2026

(54) MULTI-FLUOROUS BLOCKMER FOR OLIGONUCLEOTIDE SYNTHESIS, AND OLIGONUCLEOTIDE SYNTHESIS METHOD USING THE SAME

(71) Applicant: NATiAS Inc., Hyogo (JP)

(72) Inventors: Masanori Kataoka, Hyogo (JP); Mamoru Hyodo, Hyogo (JP)

(73) Assignee: NATIAS INC., Hyogo (JP)

( * ) Notice: Subject to any disclaimer, the term of this patent is extended or adjusted under 35 U.S.C. 154(b) by 979 days.

(21) Appl. No.: 17/595,613

(22) PCT Filed: May 21, 2020

(86) PCT No.: PCT/JP2020/020203
§ 371 (c)(1),
(2) Date: Nov. 19, 2021

(87) PCT Pub. No.: WO2020/235658
PCT Pub. Date: Nov. 26, 2020

(65) Prior Publication Data
US 2022/0235089 A1 Jul. 28, 2022

(30) Foreign Application Priority Data
May 21, 2019 (JP) ................................ 2019-095591

(51) Int. Cl.
*C07H 21/04* (2006.01)
*C07H 19/06* (2006.01)
*C07H 19/10* (2006.01)

(52) U.S. Cl.
CPC ............ *C07H 21/04* (2013.01); *C07H 19/06* (2013.01); *C07H 19/10* (2013.01)

(58) Field of Classification Search
CPC ................................ C07H 19/06; C07H 19/16
See application file for complete search history.

(56) References Cited

U.S. PATENT DOCUMENTS

| | | | |
|---|---|---|---|
| 2008/0076776 A1 | 3/2008 | Higginbottom et al. |
| 2009/0048203 A1 | 2/2009 | Cavero-Tomas et al. |
| 2014/0065223 A1 | 3/2014 | Schäfer |
| 2019/0169223 A1 | 6/2019 | Sugawara |

FOREIGN PATENT DOCUMENTS

| | | |
|---|---|---|
| EP | 3378869 A1 | 9/2018 |
| JP | 2008-516938 | 5/2008 |
| JP | 2009-541438 | 11/2009 |
| JP | 2014-510743 | 5/2014 |
| WO | WO 2005/070859 | 8/2005 |
| WO | 2006040558 A1 | 4/2006 |
| WO | 2006081035 A1 | 8/2006 |

(Continued)

OTHER PUBLICATIONS

Reg. No. 497252-29-6, which entered STN on Mar. 10, 2003. (Year: 2003).*
Hayakawa, J. Am. Chem. Soc. 1998, 120, 12395-12401. (Year: 1998).*
Ohkubo, J. Am. Chem. Soc. Vol. 126, No. 35, 2004. (Year: 2004).*
International Search Report for International Application No. PCT/JP2020/020203, "Multi-Fluorous Blockmer Used in Oligonucleotide Synthesis and Oligonucleotide Synthesis Method Using Same", dated Jun. 23, 2020.
Pearson, W.H., et al., "Fluorous Affinity Purification of Oligonucleotides", J. Org. Chem., 2005, 70, 7114-7122.

(Continued)

*Primary Examiner* — Layla D Berry
(74) *Attorney, Agent, or Firm* — Hamilton, Brook, Smith & Reynolds, P.C.

(57) ABSTRACT

Provided are a multi-fluorous blockmer using a readily available fluorous tag and capable of reducing burdens of purification, and an oligonucleotide synthesis method using the same. A multi-fluorous blockmer represented by the formula is synthesized: wherein B is a natural or modified nucleobase; $R^1$ is a protecting group that can be removed for deprotection under acidic or neutral conditions; $R^3$ is a protecting group for phosphate; Pro is unprotected, protected, or F-protector, wherein F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; X is O or S; 1 is an integer of 0 to 58; $R^7$ is $(C{=}O)(CH_2)_2(C{=}O)(CH_2)_n(CF_2)_mCF_3$ or a silyl protecting group, wherein n is 1 or 2 and m is an integer of 1 to 20.

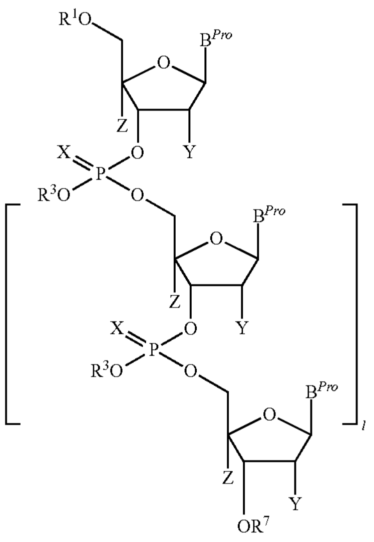

10 Claims, 6 Drawing Sheets

(56) References Cited

FOREIGN PATENT DOCUMENTS

| | | | |
|---|---|---|---|
| WO | 2008000745 | A2 | 1/2008 |
| WO | WO 2017/086397 | | 5/2017 |
| WO | 2019036029 | A1 | 2/2019 |
| WO | WO 2019/042888 | | 3/2019 |

OTHER PUBLICATIONS

Tripathi, S., et al., "Fluorous Silyl Protecting Group for 5'-Hydroxyl Protection of Oligonucleosides", Organic Preparations and Procedures Int., 37(3), 257-263 (2005).

Supplementary Partial European Search Report for EP Application No. 20809071, "Multi-Fluorous Blockmer Used in Oligonucleotide Synthesis and Oligonucleotide Syntheses Method Using Same" dated: Oct. 11, 2022.

* cited by examiner

MULTI-FLUOROUS BLOCKMER FOR OLIGONUCLEOTIDE SYNTHESIS, AND OLIGONUCLEOTIDE SYNTHESIS METHOD USING THE SAME

RELATED APPLICATIONS

This application is the U.S. National Stage of International Application No. PCT/JP2020/020203, filed May 21, 2020, which designates the U.S., published in Japanese, and claims priority under 35 U.S.C. § 119 or 365(c) to Japanese Application No. 2019-095591, filed May 21, 2019. The entire teachings of the above applications are incorporated herein by reference.

TECHNICAL FIELD

The present invention relates to a multi-fluorous blockmer in oligonucleotide synthesis, and an oligonucleotide synthesis method using the same.

BACKGROUND ART

More and more attention has been focused in recent years on nucleic acid drugs having natural or modified oligonucleotide as basic structure. To obtain nucleic acid drugs designed so as to achieve intended effect, chemical synthesis methods are widely used.

Widely known as one of such chemical synthesis methods are liquid-phase synthesis methods, which allow all reactions to proceed in a liquid phase, and are used in synthesis of relatively short oligonucleotides. Attempts have been recently made to apply a fluorous tag (a substituent favoring fluorocarbon) to such a liquid-phase synthesis method (PTL 1, PTL 2).

CITATION LIST

Patent Literature

[PTL 1] PCT International Publication No. WO 2005/070859

[PTL 2] PCT International Publication No. WO 2017/086397

SUMMARY OF INVENTION

Technical Problem

In conventionally used liquid-phase synthesis methods, dozens of steps of reactions, including coupling reaction between phosphoramidite and nucleoside and deprotection reaction to give a next reaction base point, are required even for synthesizing relatively short oligonucleotides. In most of the steps, purification using column chromatography or the like is required. Purification is complicated in most cases, and hence it is not easy to synthesize a large amount of oligonucleotides with any conventionally used liquid-phase synthesis method.

The fluorous tags used in PTL 1, PTL 2, and so on have complicated structure and are not readily available, thus resulting in high cost.

The present invention was made in view of such circumstances, and an object of the present invention is to provide a multi-fluorous blockmer, for oligonucleotide synthesis, using a readily available fluorous tag and being capable of reducing burdens of purification, and an oligonucleotide synthesis method using the same.

Solution to Problem

To solve the above problems, the multi-fluorous blockmer for oligonucleotide synthesis and oligonucleotide synthesis method using the same according to the present invention employ the following means.

A first aspect of the present invention is a protected nucleoside represented by formula (I):

(I)

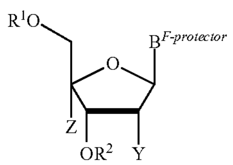

wherein B is a natural or modified nucleoside base; $R^1$ and $R^2$ are each independently H or a protecting group that can be removed for deprotection under acidic, basic, or neutral conditions; F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y.

A second aspect of the present invention is a 5'-end-protected nucleoside phosphoramidite represented by formula (II):

(II)

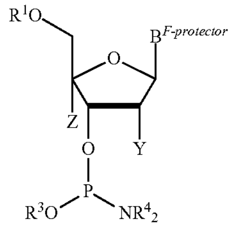

wherein B is a natural or modified nucleoside base; $R^1$ is a protecting group that can be removed for deprotection under acidic, basic, or neutral conditions; $R^3$ is a protecting group for phosphate, preferably $CH_2CH_2CN$, $CH_2CH{=}CH_2$, $OCH_3$, or $CH_2(CH_2)_xYG$, wherein Y is NH or S, G is allyl or an acyl group, and x is 0 to 3, or is taken together with one of the groups of $R^4$ bonding to the nitrogen atom bonding to the phosphorous atom to form a ring; $R^4$ is a substituted or unsubstituted aliphatic group or a substituted or unsubstituted aromatic group; F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y.

A third aspect of the present invention is a fluorous blockmer phosphoramidite represented by formula (III):

(III)

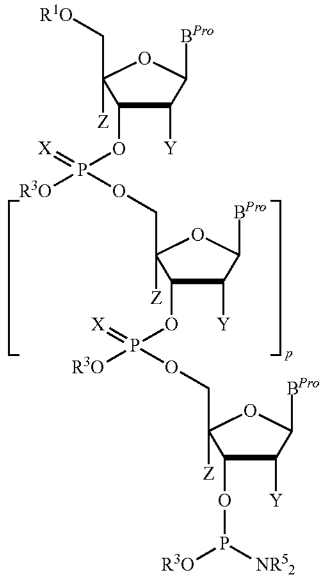

In formula (III), B is a natural or modified nucleoside base; $R^1$ is a protecting group that can be removed for deprotection under acidic, basic, or neutral conditions; $R^3$ is a protecting group for phosphate, preferably $CH_2CH_2CN$, $CH_2CH{=}CH_2$, $OCH_3$, or $CH_2$ $(CH_2)_tRG$, wherein R is NH or S, G is allyl or an acyl group, and t is 0 to 3, or is taken together with one of the groups of $R^5$ bonding to the nitrogen atom bonding to the phosphorous atom forming the phosphoramidite moiety to form a ring; $R^5$ is a substituted or unsubstituted aliphatic group or a substituted or unsubstituted aromatic group; Pro is unprotected, a protecting group for a nucleoside base, or F-protector, wherein F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is. N, wherein n is 1 or 2 and m is an integer of 1 to 20; X is O or S; p is an integer of 0 to 27; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y. The fluorous blockmer phosphoramidite represented by formula (III) has at least one group of F-protector at any of the groups of Pro, $R^1$, and $R^3$.

A fourth aspect of the present invention is a multi-fluorous blockmer represented by formula (IV):

(IV)

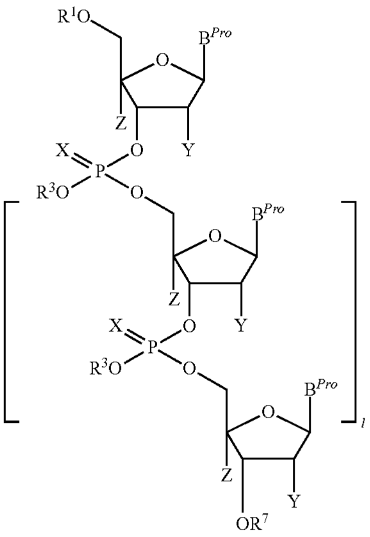

In formula (IV), B is a natural or modified nucleoside base; $R^1$ is a protecting group that can be removed for deprotection under acidic, basic, or neutral conditions; $R^3$ is a protecting group for phosphate, preferably $CH_2CH_2CN$, $CH_2CH{=}CH_2$, $OCH_3$, or $CH_2$ $(CH_2)_tRG$, wherein R is NH or S, G is allyl or an acyl group, and t is 0 to 3; Pro is unprotected, a protecting group for a nucleoside base, or F-protector, wherein F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; X is O or S; 1 is an integer of 0 to 58; $R^7$ is $(C{=}O)(CH_2)_2(C{=}O)(CH_2)_n(CF_2)_mCF_3$ or a, silyl protecting group, wherein n is 1 or 2 and m is an integer of 1 to 20; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y. The multi-fluorous blockmer represented by formula (IV) has at least one group of F-protector at any of the groups of Pro, $R^1$, and $R^3$.

A fifth aspect of the present invention is a method for synthesizing the multi-fluorous blockmer represented by formula (IV), the method including a step of performing coupling reaction between the fluorous blockmer phosphoramidite represented by formula (III) or a 5'-end-protected nucleoside H-phosphonate represented by formula (II') and a nucleoside represented by formula (V) with a fluorous anchor bonding to the 3'-end of the nucleoside. In formulas (II') and (V), B is a natural or modified nucleoside base; $R^1$ is a protecting group that can be removed for deprotection under acidic, basic, or neutral conditions; F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y; $R^7$ is $(C{=}O)(CH_2)_2(C{=}O)(CH_2)_n(CF_2)_mCF_3$ or a silyl protecting group, wherein n is 1 or 2 and m is an integer of 1 to 20.

(II')

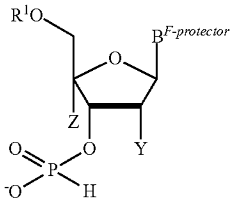

(V)

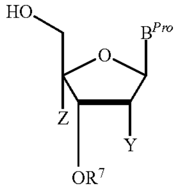

Advantageous Effects of Invention

Synthesis of oligonucleotide by using the nucleoside with the fluorous-protected base moiety, 5'-end-protected nucleoside phosphoramidite with the fluorous-protected base moiety, and the multi-fluorous blockmer according to the present invention can change solubility of intermediates in oligonucleotide synthesis and reduce burdens of purification through adjustment of the structure of the fluorous anchor and the number of molecules thereof to be introduced. Thereby, oligonucleotide can be synthesized with a more versatile method.

DESCRIPTION OF EMBODIMENTS

Figure 1:
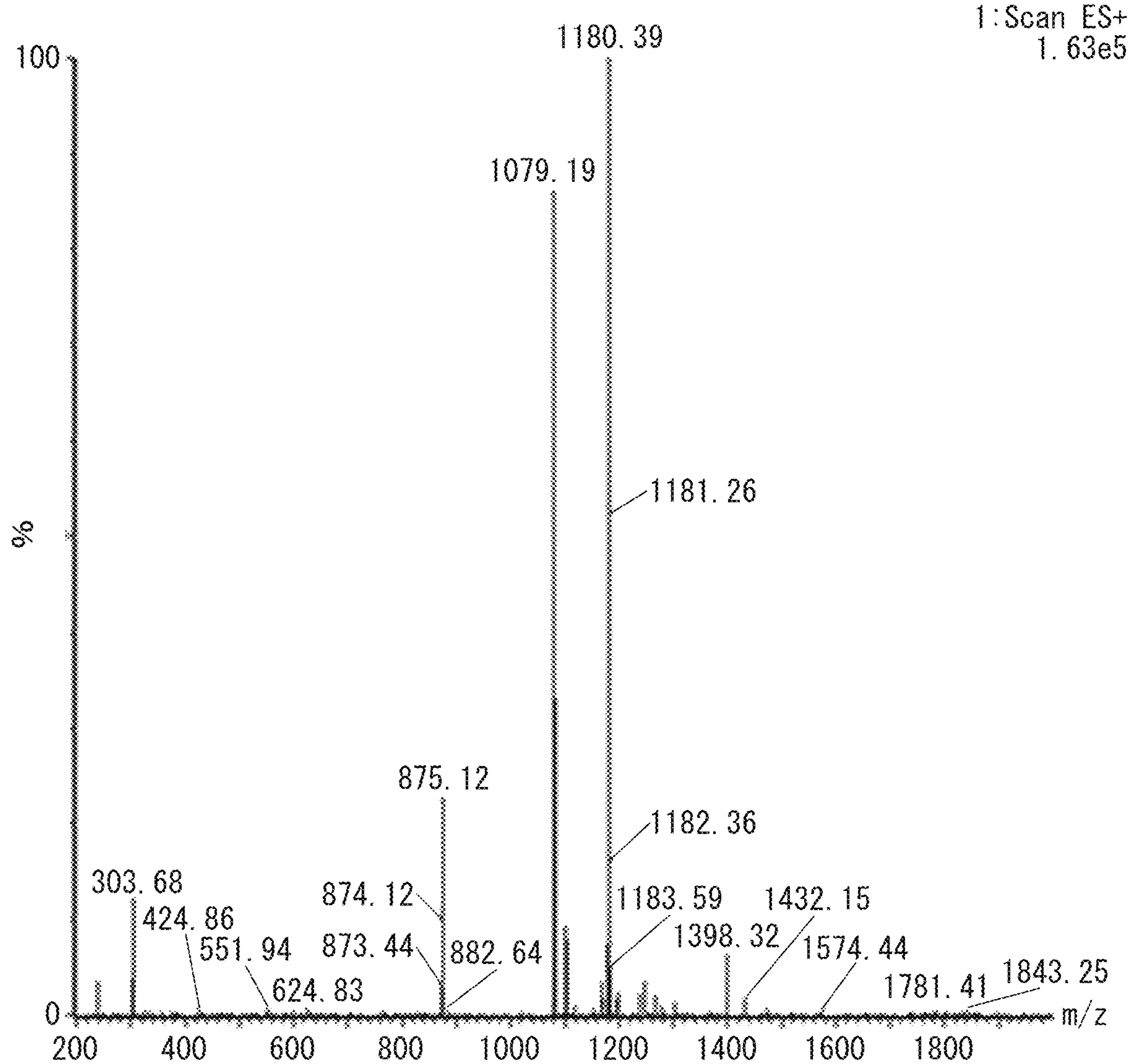
FIG. 1 shows an ESI-TOF mass spectrum for compound 6 obtained in Examples of the present invention.

Hereinafter, embodiments of the multi-fluorous blockmer for oligonucleotide synthesis and oligonucleotide synthesis method using the same according to the present invention will be described.

A protected nucleoside in the first embodiment has a structure represented by formula (I).

(I)

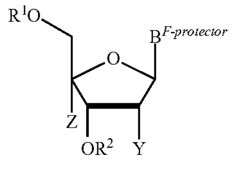

In formula (I), B is a natural or modified nucleoside base; $R^1$ and $R^2$ are each independently H or a protecting group that can be removed for deprotection under acidic, basic, or neutral conditions; F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y. Examples of the Z—Y bond include a substituted or unsubstituted C2 to C6 alkylene group, —S—, —CO—, —CS—, —COO—, —OCONR$^6$— ($R^6$ is H or a C1 to C6 alkyl group), —CONR$^6$—, and —CSNR$^6$—.

The protected nucleoside shown by formula (I) can be synthesized by (1) reacting the base moiety of a nucleoside in which 3',5'-hydroxy groups have been protected, with a commercially available fluorous alcohol to protect the base, and (2) deprotecting the protecting groups for the 3',5'-hydroxy groups of the compound obtained in (1).

Protection of the base moiety of the protected nucleoside shown in formula (I) can be carried out by applying Mitsunobu reaction or reaction using benzenesulfonic acid chloride with commercially available fluorous alcohol. In the present embodiment, 1H,1H,2H,2H-nonafluoro-1-hexanol, 1H,1H,2H,2H-tridecafluoro-1-octanol, 1H,1H-pentadecafluoro-1-octanol, or the like can be used. Because commercially available fluorous alcohol can be used, the protected nucleoside shown in formula (I) can be synthesized in a simpler manner with lower cost than in conventional methods. Specific examples of the nucleoside derivative with F-protector introduced thereinto include the following compounds.

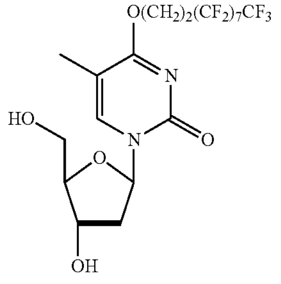

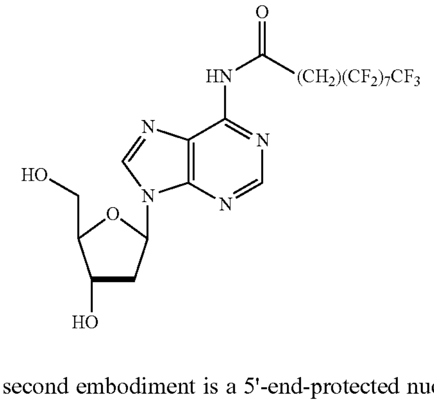

The second embodiment is a 5'-end-protected nucleoside phosphoramidite represented by formula (II).

(II)

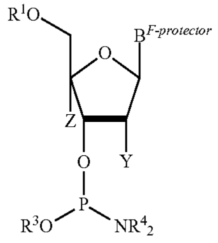

In formula (II), B is a natural or modified nucleoside base; $R^1$ is a protecting group that can be removed for deprotection under acidic, basic, or neutral conditions; $R^3$ is a protecting group for phosphate, preferably $CH_2CH_2CN$, $CH_2CH{=}CH_2$, $OCH_3$, or $CH_2$ $(CH_2)_xYG$, wherein Y is NH or S, G is allyl or an acyl group, and x is 0 to 3, or is taken together with one of the groups of $R^4$ bonding to the nitrogen atom bonding to the phosphorous atom to form a ring; $R^4$ is a substituted or unsubstituted aliphatic group or a substituted or unsubstituted aromatic group; F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y. Examples of the Z—Y bond are the same as those for the compound represented by formula (I).

The 3'-phosphoramidite shown in formula (II) can be synthesized by (1) selectively protecting the 5'-hydroxy group of the 3',5'-unprotected nucleoside represented by formula (I) with a known method, and (2) reacting the 5'-protected 3'-unprotected nucleoside obtained in (1) with a phosphitylating agent such as $NCCH_2CH_2OP[N(i\text{-}C_3H_7)_2]_2$ and $CH_2{=}CHCH_2OP[N(i\text{-}C_3H_7)_2]_2$. Step (2) can be carried out with a known method.

The third embodiment is a fluorous blockmer phosphoramidite represented by formula (III).

(III)

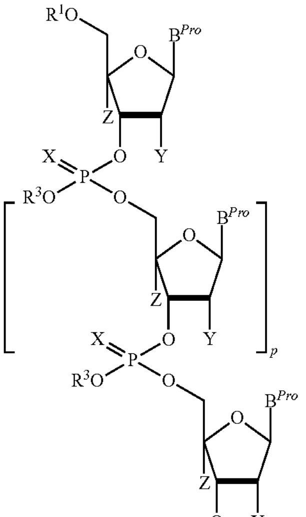

In formula (III), B is a natural or modified nucleoside base; $R^1$ is a protecting group that can be removed for deprotection under acidic, basic, or neutral conditions; $R^3$ is a protecting group for phosphate, preferably $CH_2CH_2CN$, $CH_2CH{=}CH_2$, $OCH_3$, or $CH_2(CH_2)_tRG$, wherein R is NH or S, G is allyl or an acyl group, and t is 0 to 3, or is taken together with one of the groups of $R^5$ bonding to the nitrogen atom bonding to the phosphorous atom forming the phosphoramidite moiety to form a ring; $R^5$ is a substituted or unsubstituted aliphatic group or a substituted or unsubstituted aromatic group; Pro is unprotected, a protecting group for a nucleoside base, or F-protector, wherein F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; X is O or S; p is an integer of 0 to 27; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y. Examples of the Z—Y bond are the same as those for the compound represented by formula (I). The fluorous blockmer phosphoramidite represented by formula (III) has at least one group of F-protector at any of the groups of Pro, $R^1$, and $R^3$. Herein, the term blockmer refers to a nucleotide unit that is a dimeric or higher multimeric nucleotide and serves as a synthesis block for forming a longer nucleotide through condensation reaction with a phosphoramidite, a nucleoside with the 3'- or 5'-hydroxy group unprotected, a nucleotide, or the like. The term multi-fluorous blockmer refers to a blockmer containing a plurality of fluorous tag moieties.

The fluorous blockmer phosphoramidite represented by formula (III) can be synthesized by (1) reacting the 5'-end-protected nucleoside phosphoramidite represented by formula (II) or a 5'-end-protected nucleoside H-phosphonate represented by formula (II') with a nucleoside represented by formula (V) with a fluorous anchor bonding to the 3'-end of the nucleoside to synthesize an intermediate, (2) removing the fluorous anchor from the nucleoside with a fluorous anchor bonding to the 3'-end of the nucleoside in the thus obtained intermediate to yield the 3'-unprotected form, (3) reacting the 3'-hydroxy group, now being unprotected, with a phosphitylating agent such as $NCCH_2CH_2OP[N(i\text{-}C_3H_7)_2]_2$ and $CH_2{=}CHCH_2OP[N(i\text{-}C_3H_7)_2]_2$ to produce the 3'-phosphoramidite, or forming the 3'-H-phosphonate, for example, under conditions for reaction with triphenylphosphite followed by hydrolysis with triethylamine or under conditions for reaction with phosphorus trichloride followed by hydrolysis, and (4) repeating steps (1) to (3) until a fluorous blockmer phosphoramidite of desired chain length is obtained. In formulas (II') and (V), B is a natural or modified nucleoside base; $R^1$ is a protecting group that can be removed for deprotection under acidic, basic, or neutral conditions; F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y; $R^7$ is $(C{=}O)(CH_2)_2(C{=}O)(CH_2)_n(CF_2)_mCF_3$ or a silyl protecting group, wherein n is 1 or 2 and m is an integer of 1 to 20.

(II')

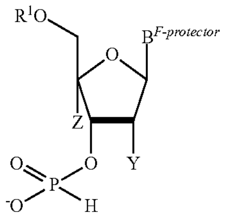

(V)

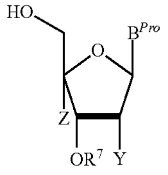

The fourth embodiment is a multi-fluorous blockmer represented by formula (IV).

(IV)

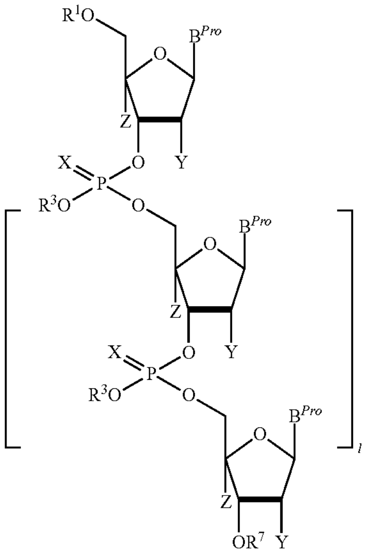

In formula (IV), B is a natural or modified nucleoside base; $R^1$ is a protecting group that can be removed for deprotection under acidic, basic, or neutral conditions; $R^3$ is a protecting group for phosphate, preferably $CH_2CH_2CN$, $CH_2CH{=}CH_2$, $OCH_3$, or $CH_2(CH_2)_tRG$, wherein R is NH or S, G is allyl or an acyl group, and t is 0 to 3; Pro, is unprotected, a protecting group for a nucleoside base, or F-protector, wherein F-protector is $O(CH_2)_n(CF_2)_mCF_3$ when the protected moiety of nucleoside base B is O, and is $NH(C{=}O)((CH_2)_n(CF_2)_mCF_3$ when the protected moiety of nucleoside base B is N, wherein n is 1 or 2 and m is an integer of 1 to 20; X is O or S; 1 is an integer of 0 to 58; $R^7$ is $(C{=}O)(CH_2)_2(C{=}O)(CH_2)_n(CF_2)_mCF_3$ or a silyl protecting group, wherein n is 1 or 2 and m is an integer of 1 to, 20; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y. Examples of the Z—Y bond are the same as those for the compound represented by formula (I).

The multi-fluorous blockmer represented by formula (IV) has at least one group of F-protector at any of the groups of Pro, $R^1$, and $R^3$.

The fifth embodiment is a method for synthesizing the multi-fluorous blockmer represented by formula (IV), the method including a step of performing coupling reaction between the fluorous blockmer phosphoramidite represented by formula (III) or a 5'-end-protected nucleoside H-phosphonate represented by formula (II') and a nucleoside represented by formula (V) with a fluorous anchor bonding to the 3'-end of the nucleoside. In formulas (II') and (V), B is a natural or modified nucleoside base; $R^1$ is a protecting group that can be removed for deprotection under acidic, basic, or neutral conditions; F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y; $R^7$ is $(C{=}O)(CH_2)_2(C{=}O)(CH_2)_n(CF_2)_mCF_3$ or a silyl protecting group, wherein n is 1 or 2 and m is an integer of 1 to 20.

(II')

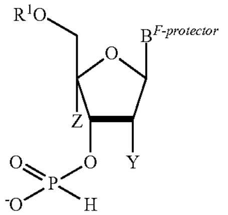

(V)

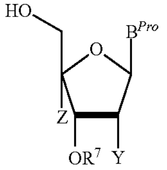

The multi-fluorous blockmer in the present embodiment can, be synthesized by (1) reacting the 5'-end-protected nucleoside phosphoramidite represented by formula (II) or the 5'-end-protected nucleoside H-phosphonate represented by formula (II') with the nucleoside represented by formula (V) with a fluorous anchor bonding to the 3'-end of the nucleoside to synthesize an intermediate, (2) removing the fluorous anchor from the nucleoside with a fluorous anchor bonding to the 3'-end of the nucleoside in the thus obtained intermediate to yield the 3'-unprotected form, (3) reacting the 3'-hydroxy group, now being unprotected, with a phosphitylating agent such as $NCCH_2CH_2OP[N(i\text{-}C_3H_7)_2]_2$ and $CH_2{=}CHCH_2OP[N(i\text{-}C_3H_7)_2]_2$ to produce the 3'-phosphoramidite, or forming the 3'-H-phosphonate, for example, by reaction with a phosphorylating agent such as triphenylphosphite, diphenylphosphite, phosphorus trichloride, and 2-chloro-4H-1,3,2-dioxaphosphorin-4-one followed by hydrolysis, and (4) repeating steps (1) to (3) until a fluorous blockmer phosphoramidite of desired chain length is obtained.

The multi-fluorous blockmer in the above embodiments can also be synthesized with an alternative method described in the following. A multi-fluorous blockmer of desired chain length can be obtained through what is called one-pot coupling of the fluorous blockmer phosphoramidite represented by formula (III), a fluorous blockmer H-phosphonate represented by formula (VI), in which the 5'-end is unprotected and H-phosphonate is present at the 3'-end, and a product obtained by deprotecting the 5'-end of the multi-fluorous blockmer represented by formula (IV). According to the chain length of a target product, the one-pot coupling reaction may be performed as follows: the 5'-end of a compound obtained by coupling of a 5'-protected fluorous blockmer phosphoramidite and a fluorous blockmer H-phosphonate is deprotected and reacted again with a fluorous blockmer phosphoramidite to synthesize a fluorous blockmer H-phosphonate of extended chain length; and the 5'-end is then deprotected and the fluorous blockmer H-phosphonate is subjected to the one-pot coupling reaction. As a further alternative method, a multi-fluorous blockmer bonding to a solid phase carrier can be synthesized by performing the above reaction by using a product obtained by bonding the 3'-end of a multi-fluorous blockmer to a solid phase carrier in place of a fluorous anchor. From any of multi-fluorous blockmers having a fluorous anchor at the 3'-end and multi-fluorous blockmers with the 3'-end bonding to a solid phase, an oligonucleotide can be obtained by performing deprotection reaction for the corresponding site. Even a modified oligonucleotide with a protecting group left only at a necessary moiety can be synthesized through selection of deprotection conditions. The multi-fluorous blockmer represented by formula (IV) has at least one group of F-protector at any of the groups of Pro, $R^1$, and $R^3$. This enables simpler separation/purification of intermediates and products through the utilization of the affinity of the multi-fluorous blockmer than in the case with use of a conventionally used protecting group.

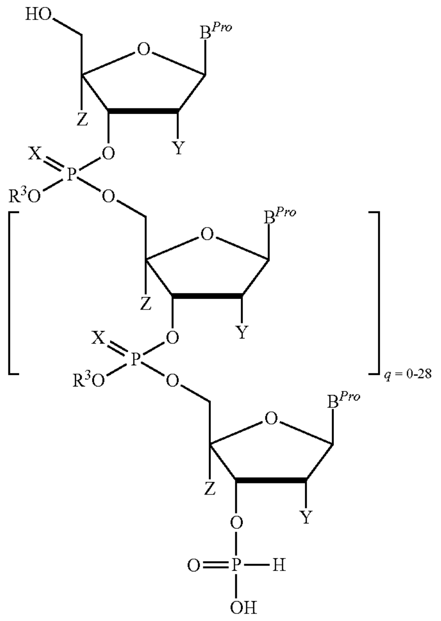

(VI)

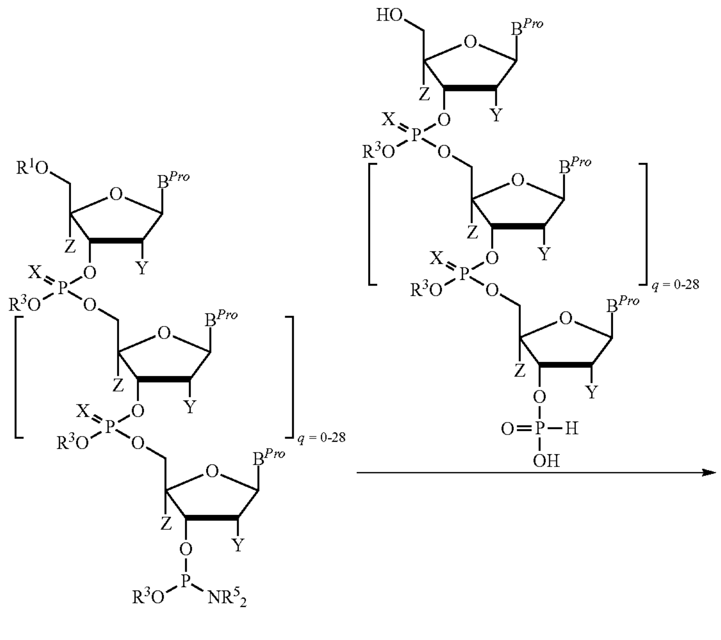

-continued
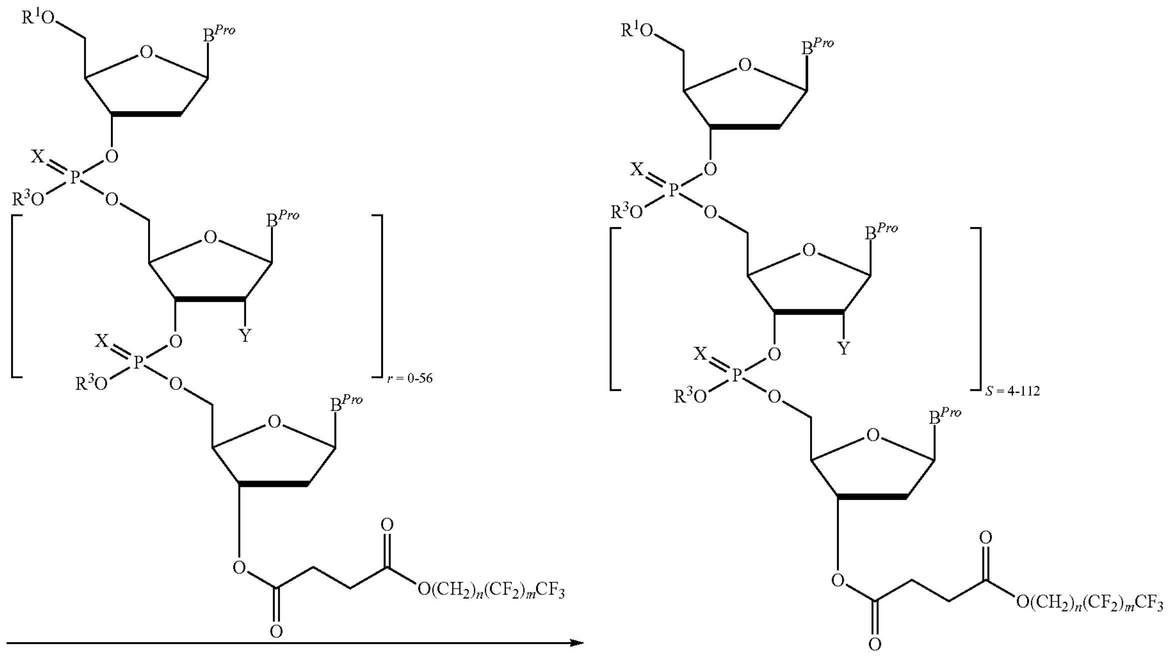
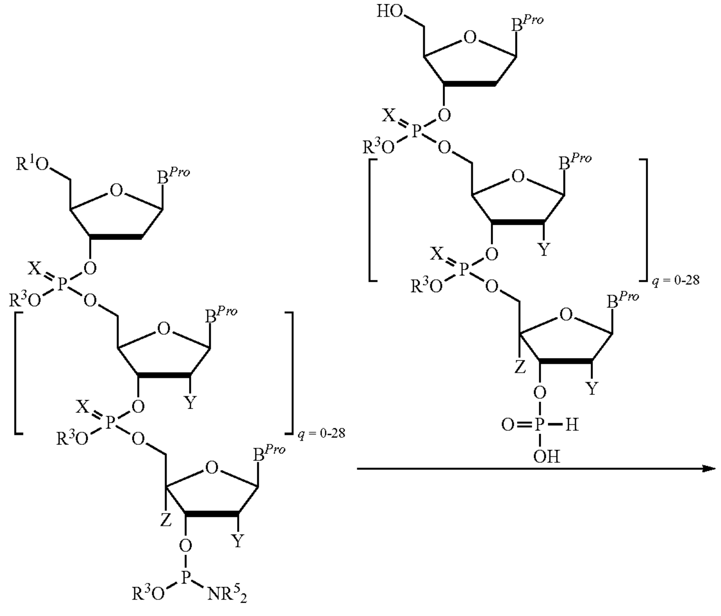
SS = solid support

-continued

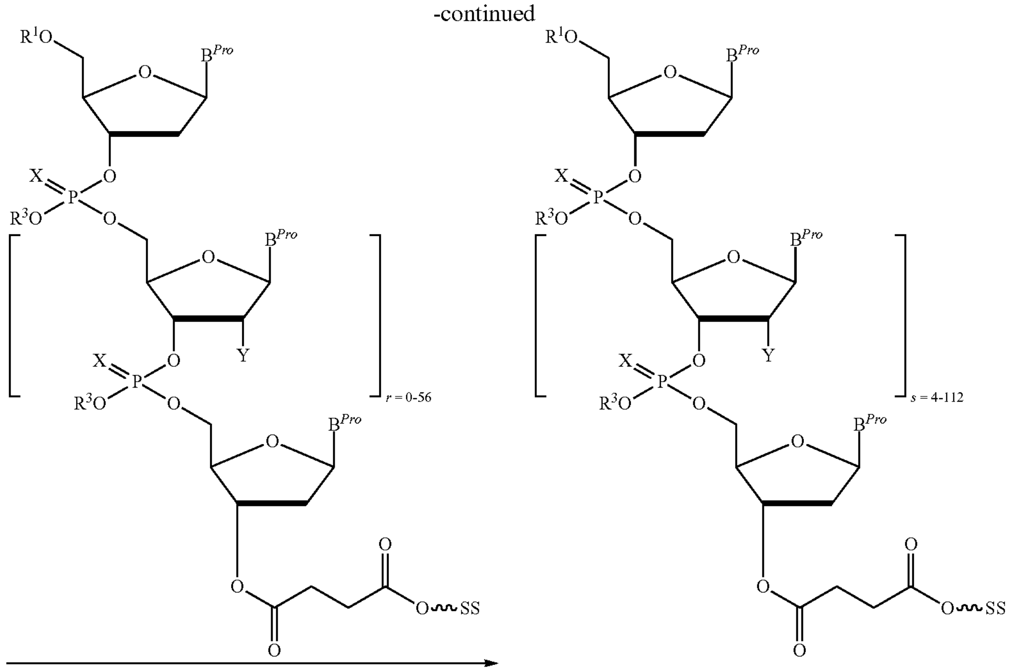

Nucleoside bases in the above embodiments include natural bases such as an adenyl group, a guanyl group, a cytosinyl group, a thyminyl group, and a uracil group, and modified bases such as a 5-methylcytosinyl group, a 5-fluorouracil group, a 7-methylguanyl group, and a 7-deazaadenyl group. The term "modified nucleoside base" herein encompasses bases having a reactive functional group such as an amino group, a carbonyl group, a hydroxyl group, and a thiol group. To such a reactive functional group, a fluorous-protecting group derived from fluorous alcohol is introduced. Examples of the protecting group to protect a nucleoside base include an acyl group, a benzoyl group, and an allyloxycarbonyl group.

Aliphatic groups in the above embodiments include saturated or unsaturated, linear or branched $C_1$-$C_{18}$ hydrocarbons and saturated or unsaturated cyclic $C_3$-$C_{18}$ hydrocarbons. Each aliphatic group is preferably a saturated or unsaturated $C_1$-$C_8$ hydrocarbon or $C_3$-$C_8$ cyclic hydrocarbon. Aromatic groups in the above embodiments include carbocyclic aromatic rings such as a phenyl group and carbocyclic aromatic rings fused with a carbocyclic aromatic ring such as a naphthyl group or non-carbocyclic aromatic ring. Each aliphatic group or aromatic group in the above embodiments may be substituted with a substituent such as a saturated or unsaturated $C_1$-$C_8$ hydrocarbon or $C_3$-$C_8$ cyclic hydrocarbon, a halogen, cyano, nitro, and an aromatic ring. Each group bonding to the nitrogen atom bonding to the phosphorus atom is preferably a linear or branched alkyl group or a secondary amino group such as pyrrolidine, diethylamine, and a morpholino group, and more preferably an isopropyl group. An alkyl group bonding to the nitrogen atom bonding to the phosphorus atom may form a ring through bonding between one end of the alkyl group and the neighboring nitrogen atom.

Any phosphate protecting group conventionally used in oligonucleotide synthesis can be used for each phosphate protecting group linking neighboring nucleosides in the above embodiments. Each protecting group is preferably $—CH_2CH_2CN$, $—CH_2CH═CH_2$, $—OCH_3$, a 2-chlorophenyl group, or a phenyl group, and, alternatively, $R^3$ and one of the groups of $R^4$ or $R^5$ bonding to the nitrogen atom bonding to the phosphorus atom may be forming a ring. Examples of protecting groups other than the above-mentioned ones include $—CH_2CH_2E$ (E: electron-withdrawing group) and a fluorine-containing protecting group that can be removed for deprotection under basic conditions.

Protecting groups for the 5'-hydroxy group in the above embodiments include protecting groups that can be removed for deprotection under acidic conditions, basic conditions, or neutral conditions. Protecting groups that can be removed for deprotection under acidic conditions include ether protecting groups with a substituted or unsubstituted trityl group, a pixyl group, and a substituted or unsubstituted tetrahydropyranyl (THP) group, and a representative example of such protecting groups is a 4,4'-dimethoxytrityl group. Examples of protecting groups removal under neutral conditions include silyl protecting groups, which specifically include a trimethylsilyl group, a triethylsilyl group, a t-butyldimethylsilyl group, a t-butyldiphenylsilyl group, and a triphenylsilyl group. Examples of protecting groups that can be removed for deprotection under basic conditions include an Fmoc group and a pivaloyl group. Examples of protecting groups other than the above-mentioned ones include alkyl groups, an acyl group, an acetyl group, a benzoyl group, a benzyl group, alkoxyalkyl groups, and a carbamoyl group.

In the above embodiments, in the step of forming a phosphoramidite on the unprotected 3'-hydroxy group, a phosphitylating agent (1.05 to 2.0 equivalents with respect to the 3'-unprotected nucleoside) and an activator (0.4 to 0.8 equivalents with respect to the 3'-unprotected nucleoside) are added to a solution of the 3'-unprotected nucleoside (0.1 to 0.4 M), which is then stirred at room temperature for 10 to 20 hours. The resulting 3'-phosphoramidite is purified by silica gel column chromatography.

In the above embodiments, after adding the activator to activate the phosphoramidite moiety to the 3'-phosphoramidite represented by formula (II) or (III), the multi-fluorous blockmer represented by formula (IV) can be obtained by coupling the nucleoside represented by formula (V) with a fluorous anchor bonding to the 3'-end of the nucleoside. Representative examples of the activator include, but are not limited to, 1H-tetrazole, S-ethylthiotetrazole, dicyanoimidazole, dichloroimidazole, and tertiary amine salts of sulfonic acid and azole. The reaction is performed in a dried solvent such as dichloromethane, acetonitrile, tetrahydrofuran, DMF, and toluene.

As an alternative method to the method of elongating base by base in synthesizing the blockmer phosphoramidite or multi-fluorous blockmer in the above embodiments, a blockmer phosphoramidite that has already been a dimer or higher multimer can be allowed to condense with the nucleoside with a fluorous anchor bonding to the 3'-end of the nucleoside to elongate by two or more bases at once.

Synthesis of the multi-fluorous blockmer to be performed with use of the blockmer phosphoramidite represented by formula (III) can be performed in a solution (hereinafter, referred to as "liquid-phase synthesis method"). After being synthesized with the above-described method, the multi-fluorous blockmer can be purified in a simple manner by column chromatography using commercially available silica gel, silica gel modified with octadecyl, diol, or the like, or silica gel for fluorous solid phase extraction. An example of commercially available silica gel for fluorous solid phase extraction is FluoroFlash silica gel 40 μm, which can be purchased from Sigma-Aldrich Co. LLC. The liquid-phase synthesis method allows larger-scale (10 to 100 times or more) synthesis than solid-phase synthesis methods, in which coupling reaction is performed on a solid-phase resin, thus enabling synthesis of a multi-fluorous blockmer for oligonucleotide synthesis with lower cost. Further, a liquid separation operation with organic solvent and water, fluorous solvent and organic solvent, or fluorous solvent and water, countercurrent chromatography with such a two-phase system, simple purification by crystallization/powderization, and so on can be applied.

Further, the affinity with silica gel for fluorous solid phase extraction can be altered by adjusting the number of molecules of the F-anchor according to the present invention to be introduced as a protecting group to the nucleoside base moieties of the multi-fluorous blockmer, in other words, by introducing the F-anchor according to the present invention to some of the nucleoside base moieties and using a conventionally used protecting group for the other nucleoside base moieties. This allows the multi-fluorous blockmer to remain on silica gel for fluorous solid phase extraction, enabling separation from reaction byproducts and excess portions of reagents in a simpler manner. The solubility in solvent can be altered even at stages of intermediates in synthesis of the multi-fluorous blockmer, and this allows purification by affinity chromatography and purification by partition with fluorous solvent/hydrocarbon organic solvent, without relying on purification by silica gel chromatography. Thus, an appropriate purification method can be selected according to the amount of the multi-fluorous blockmer according to the present invention to be synthesized and the chain length thereof.

In synthesis of oligonucleotide using the multi-fluorous blockmer represented by formula (IV), for example, the phosphite can be reacted not with an oxidizing agent but with a sulfurizing agent to convert some of the phosphate moieties into thiophosphate at the stage of synthesis of the multi-fluorous blockmer. Accordingly, pre-synthesis of a multi-fluorous blockmer to which thiophosphate has been introduced in the course of blockmer synthesis enables synthesis of an oligonucleotide in which thiophosphate has been correctly introduced to targeted positions.

Examples below are for description and illustration of the embodiments of the present invention. A nucleoside phosphoramidite with the fluorous-protected-base moiety, which is an example of the compound represented by formula (II), was produced in accordance with a procedure shown in Example 1. A multi-fluorous blockmer, which is an example of the compound represented by formula (IV), was produced in accordance with a procedure shown in Example 2. Further, synthesis of an oligonucleotide nonadecamer was performed by using hexameric phosphoramidite as blockmer phosphoramidite, which is an example of the compound represented by formula (III), and a multi-fluorous blockmer, which is an example of the compound represented by formula (IV).

(Example 1) Synthesis of Phosphoramidite with Nucleoside Having Fluorous-Protected Base Moiety Step-1: Fluorous Protection of Base Moiety of 3',5'-Protected Nucleoside

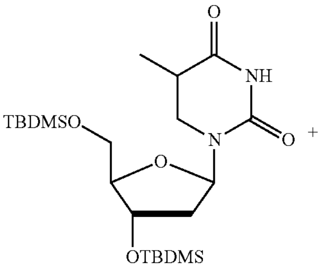

1

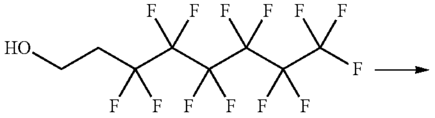

2

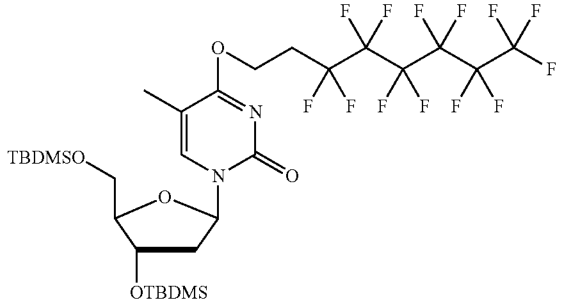

3

In tetrahydrofuran (25 mL), 3',5'-bis-O-tert-butyldimethylsilylthymidine 1 (2.4 g, 5.0 mmol), which can be synthesized with a known method, was dissolved, and the temperature was set to 0° C. Thereto, triphenylphosphine (1.4 g, 5.5 mmol), 40% diethyl azodicarboxylate/toluene solution (2.5 mL, 5.5 mmol), and 1H,1H,2H,2H-tridecafluoro-1-octanol 2 (2.0 g, 1.2 mL, 5.5 mmol) were added, and the resultant was stirred for 12 hours. The reaction solution was directly concentrated, a solid precipitated was collected through filtration, the solid was washed with hexane:ethyl acetate=1:1 solution, and the resulting solution was then concentrated again to afford a crude product. This was subjected to silica gel column chromatography. A fraction eluted with hexane:ethyl acetate=4:1 was collected to afford 3.3 g (4.1 mmol) of 3',5'-bis-O-tert-butyldimethylsilyl-4-O-1H,1H,2H,2H-tridecafluoro-1H-octylthymidine 3, as the target, at a yield of 81%. ESI-TOF Mass: 840.3 [M+Na$^+$]$^+$.

Step 2: 3',5'-Deprotection of 3',5'-Protected Nucleoside with Fluorous-Protected Base Moiety

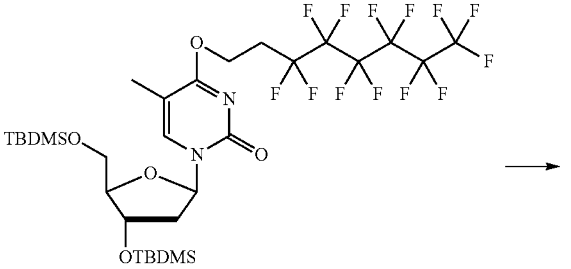

3

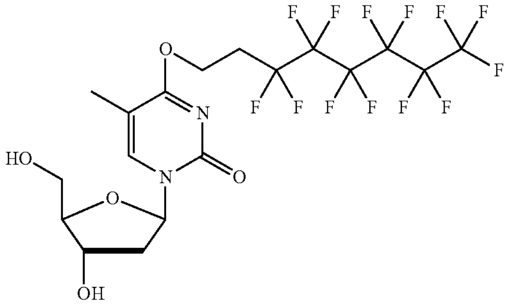

4

Compound 3 (1.6 g, 2.0 mmol) was dissolved in tetrahydrofuran (32 mL), and the temperature was set to 0° C. Thereto, acetic acid (120 mg, 0.11 mL, 2.0 mol) and 1.0 M tetrabutylammonium fluoride/tetrahydrofuran solution (8.0 mL, 8.0 mmol) were added, and the resultant was stirred for 12 hours. The reaction solution was partially concentrated to a volume of about 5 mL, and the resulting reaction mixture was subjected to silica gel column chromatography. A fraction eluted with ethyl acetate was collected to afford 1.2 g (2.0 mmol) of 4-O-1H,1H,2H,2H-tridecafluoro-1H-octylthymidine 4, as the target, at a yield of 98%. ESI-TOF Mass: 612.0 [M+Na$^+$]$^+$.

Step 3: 5'-Protection of 3',5'-Unprotected Nucleoside with Fluorous-Protected Base Moiety

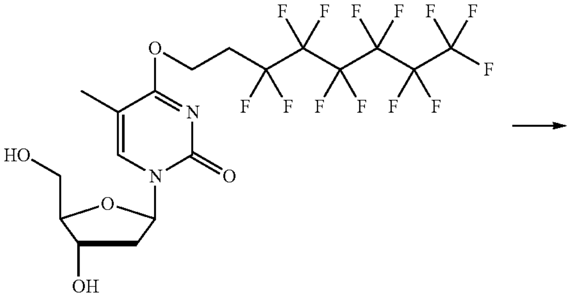

4

-continued

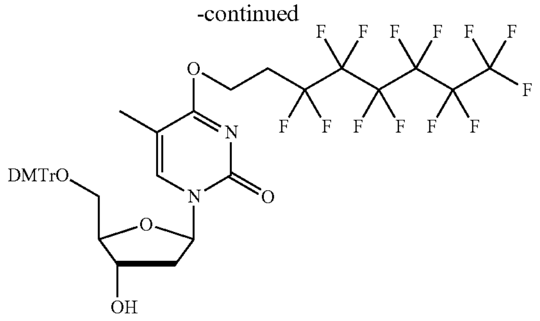

5

Compound 4 (1.2 g, 2.0 mmol) was dissolved in dimethylformamide:pyridine=1:1 solution (10 mL), to which 4,4-dimethylaminopyridine (24 mg, 0.20 mmol) and dimethoxytrityl chloride (810 mg, 2.4 mmol) were added, and the resultant was stirred for 90 minutes. Ethyl acetate (100 mL) was added to the reaction solution, and the organic layer was washed three times with 0.2 N aqueous solution of hydrochloric acid. The organic layer was dried over sodium sulfate and filtered, and the solvent was then distilled off to afford a crude product. This was subjected to silica gel column chromatography, and a fraction eluted with hexane:ethyl acetate=7:3 was collected to afford 1.5 g (1.7 mmol) of 5'-dimethoxytrityl-4-O-1H,1H,2H,2H-tridecafluoro-1H octylthymidine 5, as the target, at a yield of 83%. ESI-TOF Mass: 914.7 [M+Na$^+$]$^+$.

Step 4: Phosphitylation of 5'-Protected 3'-Unprotected Nucleoside with Fluorous-Protected Base Moiety

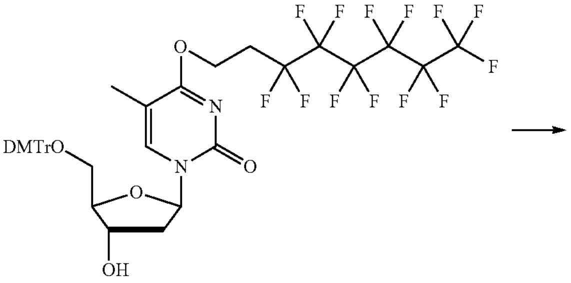

5

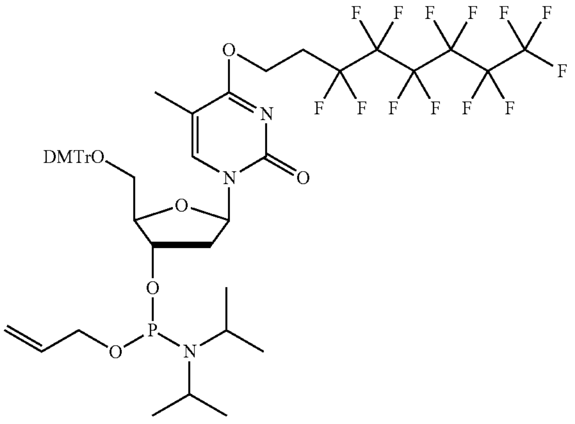

6

Compound 5 (1.4 g, 1.6 mmol) was dissolved in dichloromethane:acetonitrile=1:1 solution (16 mL), to which 1H-tetrazole (80 mg, 1.1 mmol) was added, and the resultant was stirred at 0° C. for 15 minutes. Thereto, allyl tetraisopropylphosphoramidite (710 mg, 0.74 mL, 2.4 mmol) was added to initiate reaction. After 15 hours, the reaction mixture was directly subjected to silica gel column chromatography, and a fraction eluted with hexane:ethyl acetate=9:1 was collected to afford 1.6 g (1.4 mmol) of allyl 5'-dimethoxytrityl-4-O-1H,1H,2H,2H-tridecafluoro-1H-octylthymidine-3'-phosphoramidite 6, as the target, at a yield of 89%. UPLC measurement showed that the purity was 97%. ESI-TOF Mass: 1079.2 $[M+H^+]^+$. FIG. 1 shows the ESI-TOF spectrum for compound 6.

(Example 2) Synthesis of Multi-Fluorous Blockmer

Step 5: Synthesis of Dimer of Nucleoside with Fluorous-Protected Base Moiety

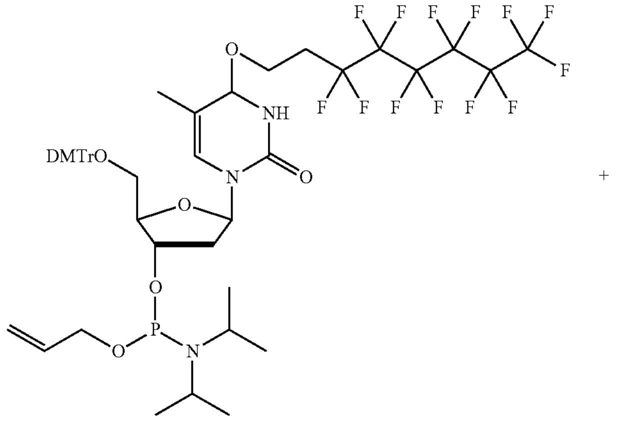

6

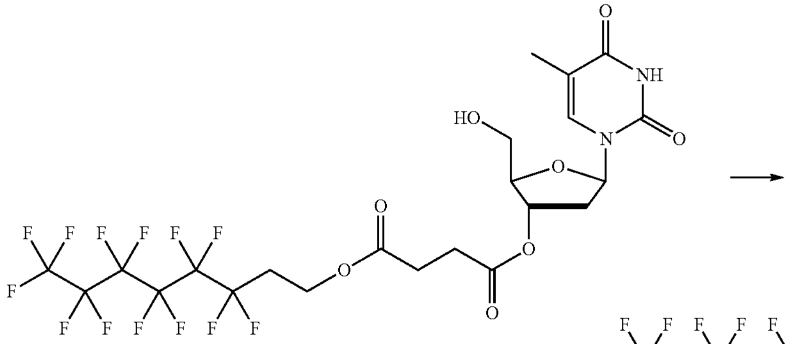

7

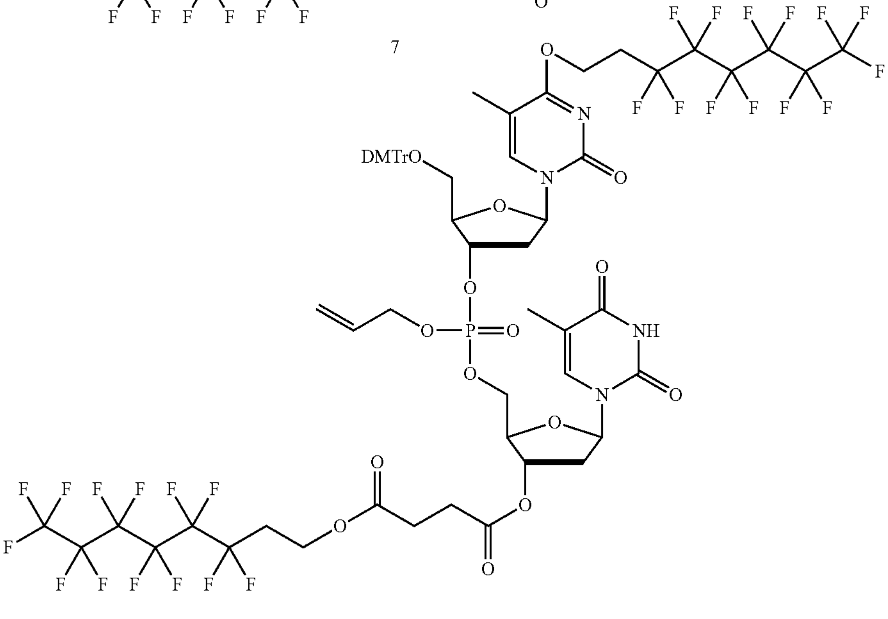

8

Figure 2:
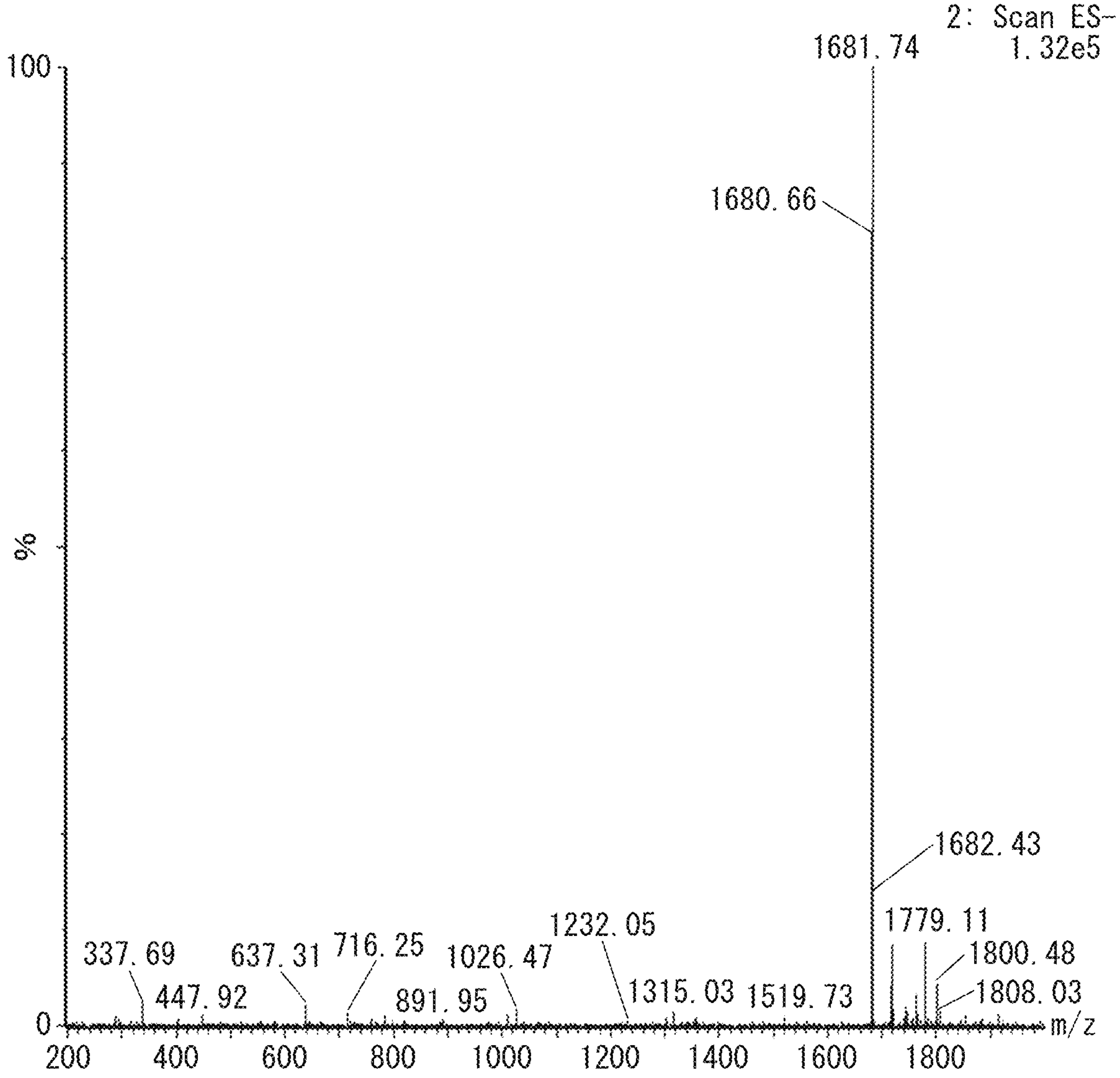
FIG. 2 shows an ESI-TOF mass spectrum for compound 8 obtained in Examples of the present invention.

Compound 6 (520 mg, 0.48 mmol) was mixed with compound 7 (280 mg, 0.40 mmol), which can be synthesized with a method described in a literature, the resultant was then vacuum-dried, and the pressure was set to normal pressure by filling there with argon gas flow. Thereto, molecular sieves 3 A (800 mg) and then dichloromethane: acetonitrile=1:1 solution (8 mL) were added, and the resultant was stirred for 2 hours. Thereto, 1H-tetrazole (110 mg, 1.6 mmol) was added, and the resultant was stirred at room temperature for 30 minutes. After checking the progression of reaction, 31 wt % 2-butanone peroxide/2,2,4-trimethyl-1,3-pentane diisobutyrate solution (0.39 mL, 0.6 mmol) was added, and the reaction was allowed to continue. After 30 minutes, the reaction mixture was filtered through a Celite, concentrated to reach a solution volume of 8 mL, and then subjected to silica gel column chromatography. A fraction eluted with hexane:ethyl acetate=2:3 was collected to afford 640 mg (0.38 mmol) of bisfluorous TT blockmer 8, as the target, at a yield of 94%. UPLC measurement showed that the purity was 98%. ESI-TOF Mass: 1680.6 $[M-H^+]^-$. FIG. 2 shows the ESI-TOF spectrum for compound 8.

(Example 3) Liquid-Phase Synthesis of Oligonucleotide Nonadecamer Using Hexameric Phosphoramidite Step 6: Condensation Reaction of Hexameric Phosphoramidite and 5'-Protected Nucleoside with 3'-Bonding Fluorous Anchor

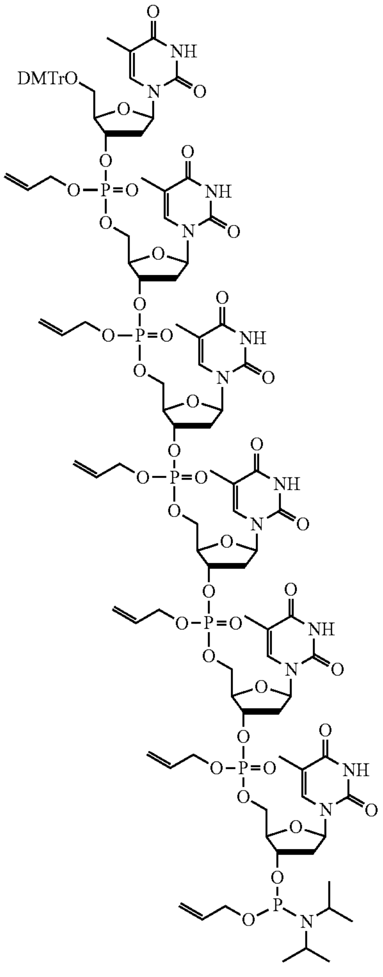

9

+

-continued

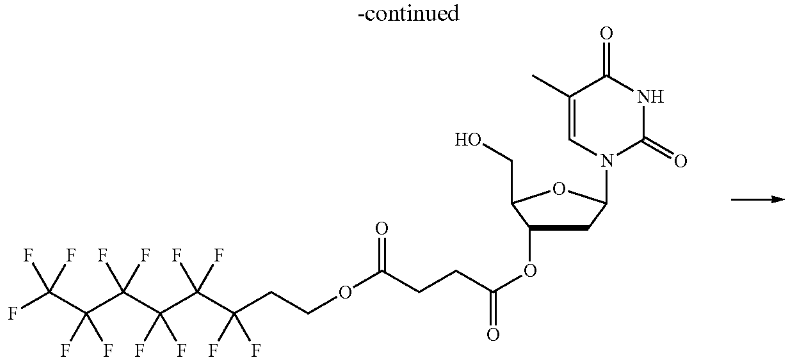

7

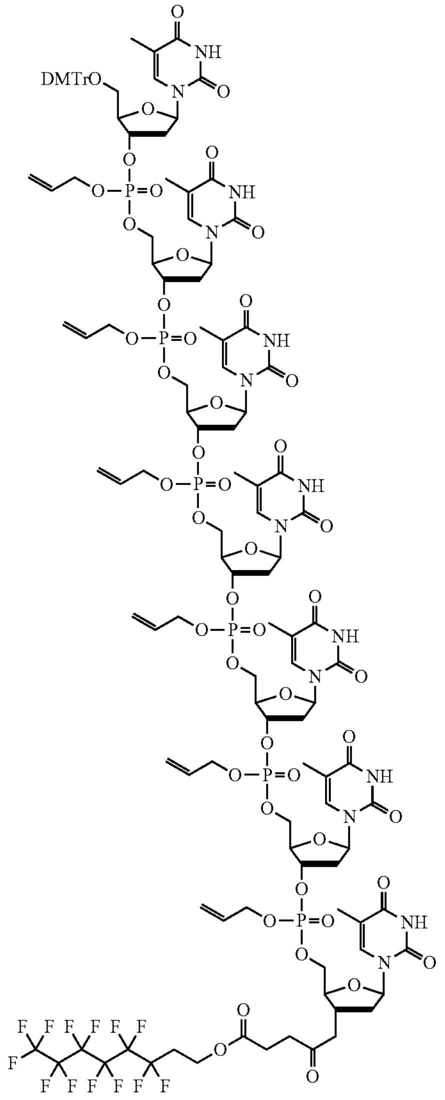

10

Compound 9 (400 mg, 0.17 mmol) was mixed with compound 7 (100 mg, 0.15 mmol), which can be synthesized with a known method, the resultant was then vacuum-dried, and the pressure was set to normal pressure by filling there with argon gas flow. Thereto, molecular sieves 3 A (600 mg) and then dichloromethane:acetonitrile=1:1 solution (6 mL) were added, and the resultant was stirred for 2 hours. Thereto, 5-ethyl-1H-tetrazole (78 mg, 0.60 mmol) was added, and the resultant was stirred at room temperature for 30 minutes. After checking the progression of reaction, 31 wt % 2-butanone peroxide/2,2,4-trimethyl-1,3-pentane diisobutyrate solution (0.15 mL, 0.30 mmol) was added, and the reaction was allowed to continue. After 30 minutes, the reaction mixture was filtered through a Celite, concentrated to reach a solution volume of 5 mL, and then subjected to silica gel column chromatography. A fraction eluted with dichloromethane:methanol=20:1 was collected to afford 260 mg (0.084 mmol) of T heptamer 10, as the target, at a yield of 56%. ESI-TOF Mass: 1552.2 $[M+2Na^{+}]^{+}$.

Step 7: 5'-Deprotection of 5'-Protected Nucleotide Heptamer with 3'-Bonding Fluorous Anchor

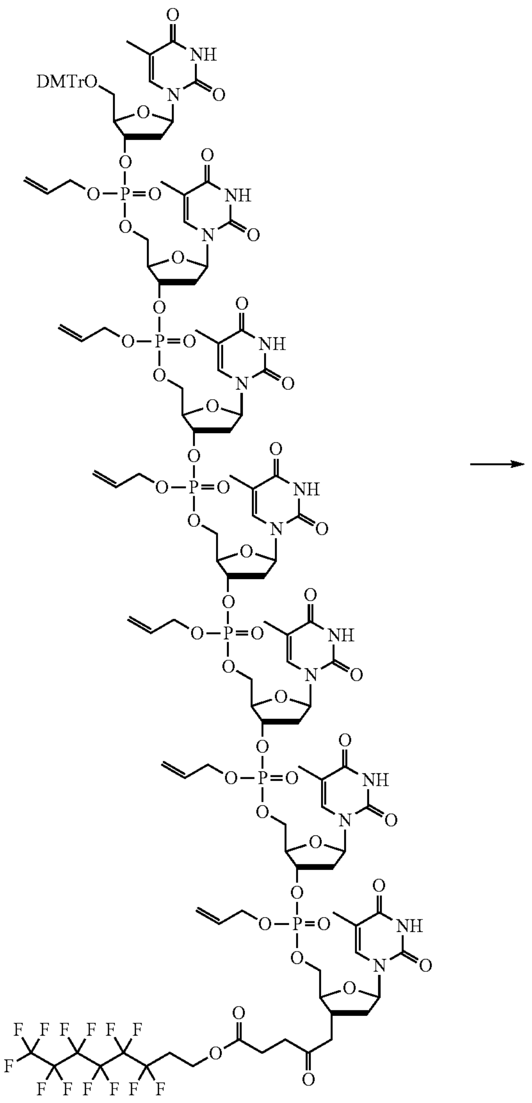

10

-continued

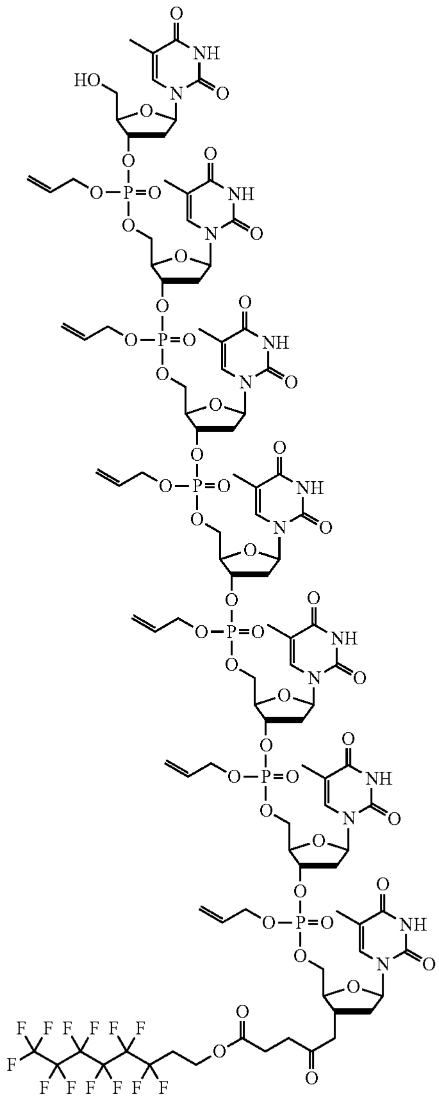

11

Compound 10 (230 mg, 0.076 mmol) was added to dichloromethane:acetonitrile=4:1 solution (4 mL) and dissolved therein, and the resultant was then soaked in an ice bath to set the temperature to 0° C. Thereto, dichloroacetic acid (200 mg, 0.13 mL, 1.5 mmol) was added, and the resultant was stirred for 30 minutes. After checking the progression of reaction, the reaction mixture was directly subjected to silica gel column chromatography. A fraction eluted with dichloromethane:methanol=13:1 was collected to afford 180 mg (0.065 mmol) of detritylated T heptamer 11, as the target, at a yield of 86%.

Step 8: Synthesis of 5'-Protected Nucleotide Tridecamer by Condensation Between 5'-Protected Hexameric Blockmer Phosphoramidite and 5'-Unprotected Nucleotide Heptamer with 3'-Bonding Fluorous Anchor
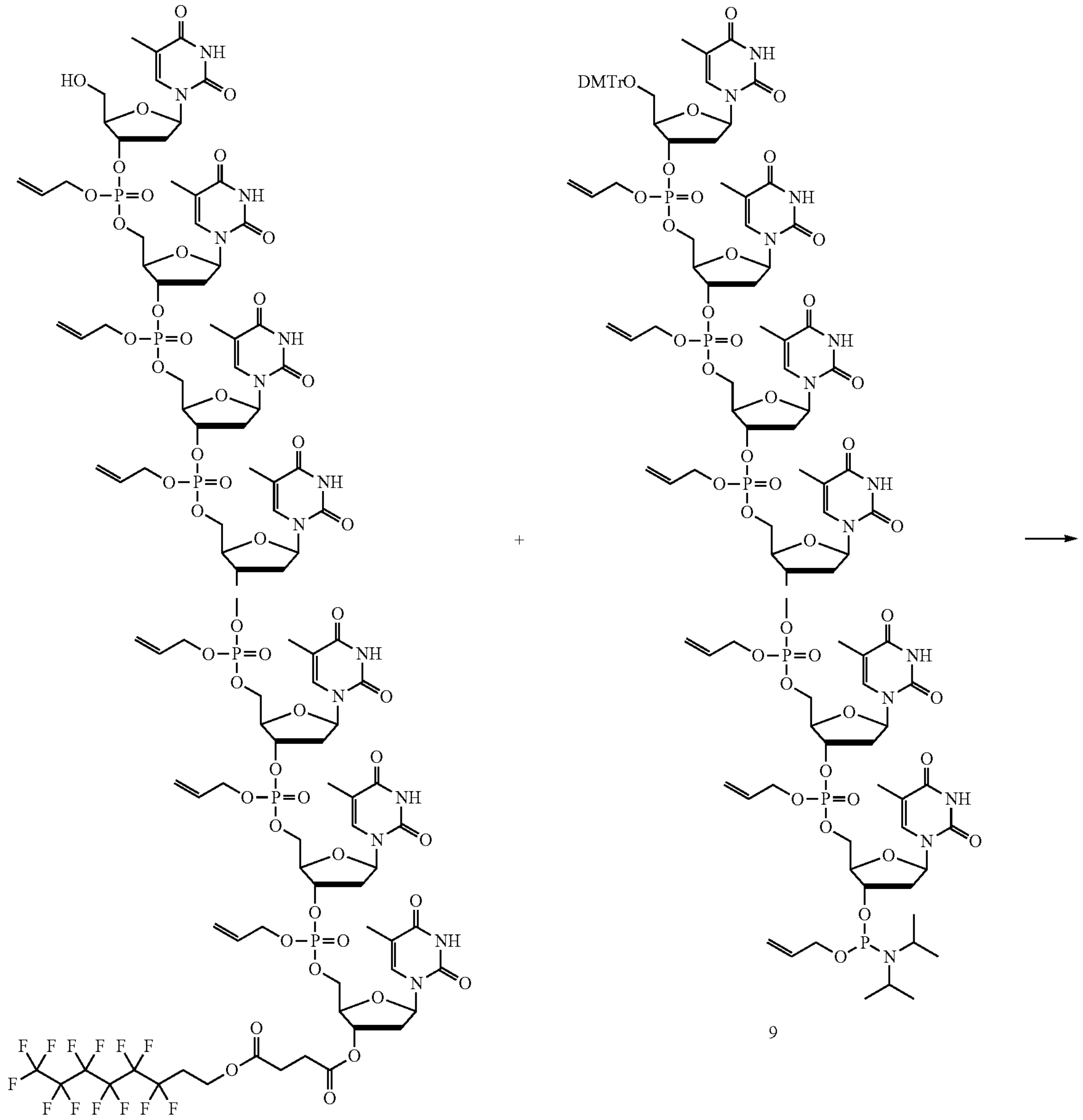
11
9

-continued
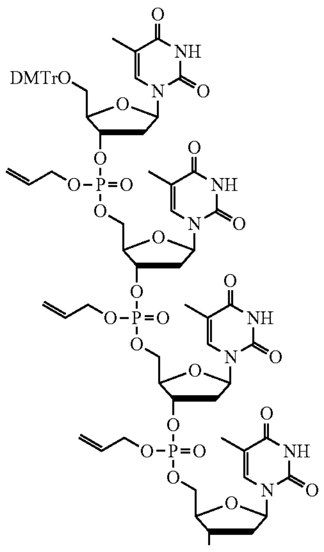
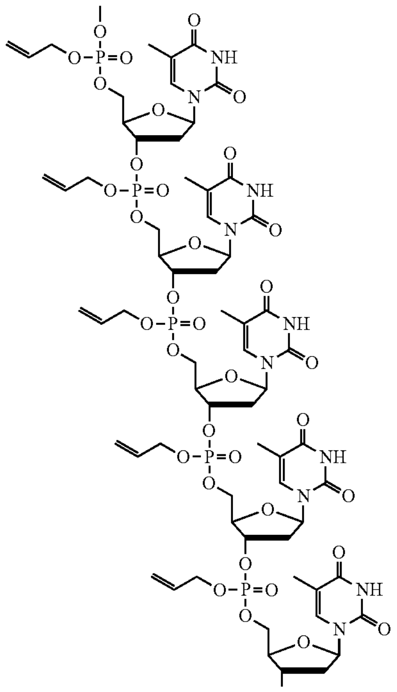

-continued

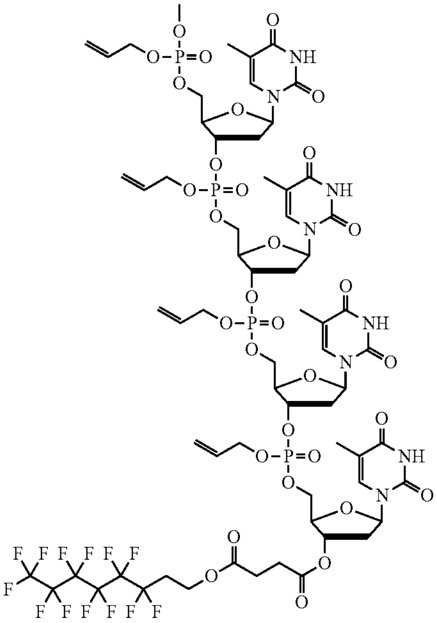

12

Compound 9 (240 mg, 0.10 mmol) and compound 11 (210 mg, 0.076 mmol) were mixed together and then vacuum-dried, and the pressure was set to normal pressure by filling there with argon gas flow. Thereto, molecular sieves 3 A (500 mg) and then dichloromethane:acetonitrile=1:1 solution (5 mL) were added, and the resultant was stirred for 2 hours. Thereto, 5-ethyl-1H-tetrazole (40 mg, 0.30 mmol) was added, and the resultant was stirred at room temperature for 30 minutes. After checking the progression of reaction, 31 wt % 2-butanone peroxide/2,2,4-trimethyl-1,3-pentane diisobutyrate solution (0.073 mL, 0.11 mmol) was added, and the reaction was allowed to continue. After 30 minutes, the reaction mixture was filtered through a Celite, concentrated to reach a solution volume of 5 mL, and then subjected to silica gel column chromatography. A fraction eluted with dichloromethane:methanol=9:1 was collected to afford 260 mg (0.051 mmol) of T tridecamer 12, as the target, at a yield of 73%.

Step 9: 5'-Deprotection of 5'-Protected Nucleotide Tridecamer

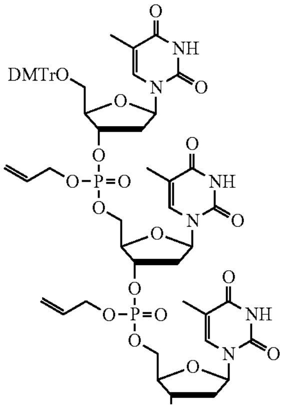

-continued
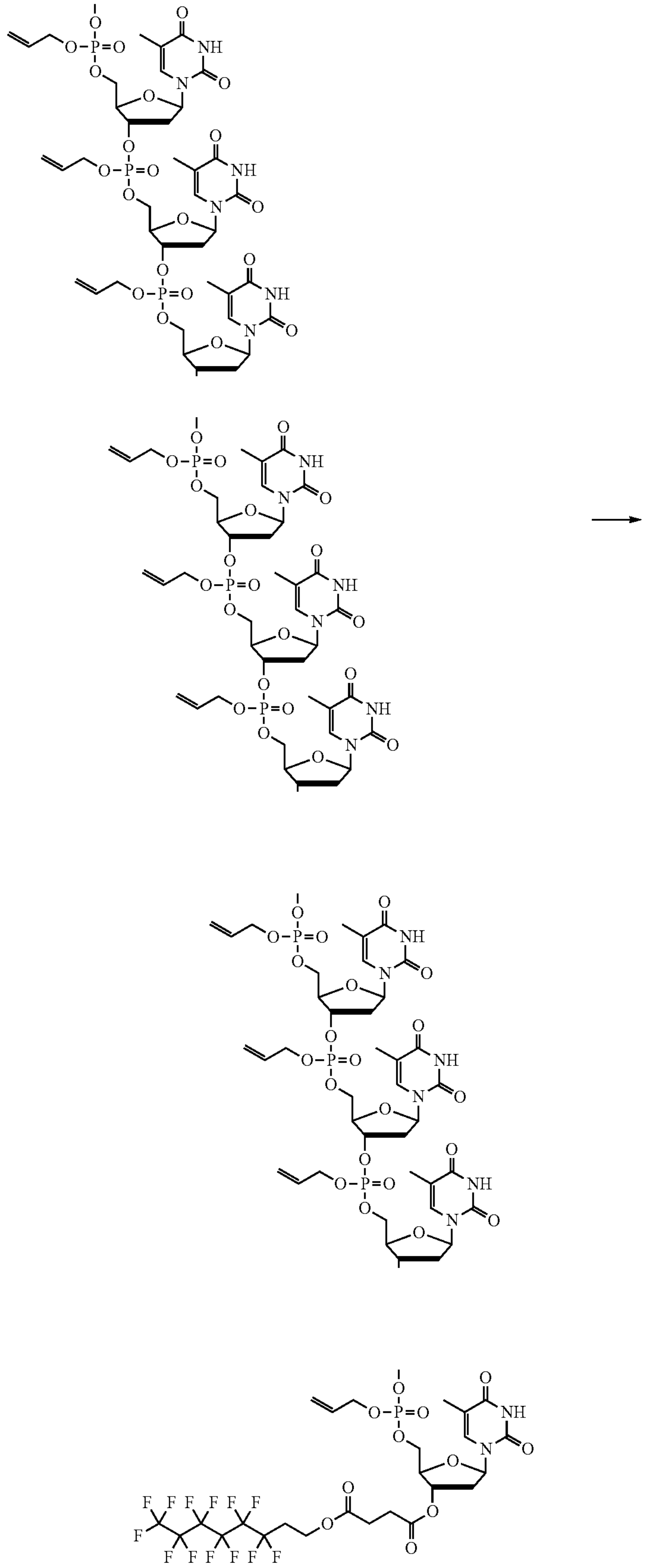
12

-continued
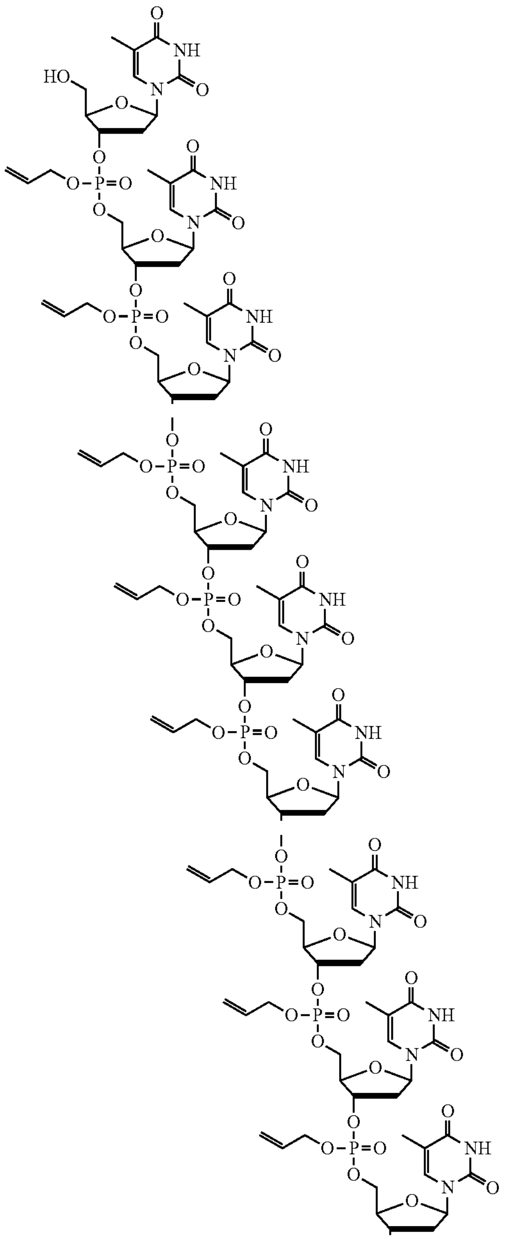
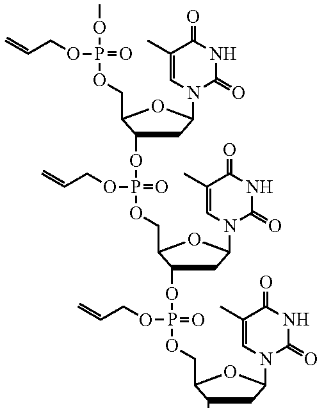

-continued

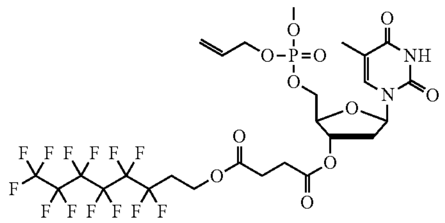

13

Compound 12 (480 mg, 0.093 mmol) was added to dichloromethane:acetonitrile=4:1 solution (4.5 mL) and dissolved therein, and the resultant was then soaked in an ice bath to set the temperature to 0° C. Thereto, dichloroacetic acid (240 mg, 0.15 mL, 1.9 mmol) was added, and the resultant was stirred for 30 minutes. After confirming the progression of reaction, the reaction mixture was directly subjected to silica gel column chromatography. A fraction eluted with dichloromethane:methanol=9:1 was collected to afford 240 mg (0.050 mmol) of detritylated T tridecamer 13, as the target, at a yield of 52%. The compound obtained was confirmed to be the target tridecamer through a process that a part of the compound obtained was subjected to ammonia hydrolysis and a molecular ion peak indicative of the T tridecamer, $[M-H^+]^-$ 3889.67 (calc.: 3889.64), was found through observation.

Step 10: Synthesis of 5'-Protected Nucleotide Nonadecamer with 3'-Bonding Fluorous Anchor by Condensation Between 5'-Protected Hexameric Blockmer Phosphoramidite and 5'-Unprotected Nucleotide Tridecamer with 3'-Bonding Fluorous Anchor

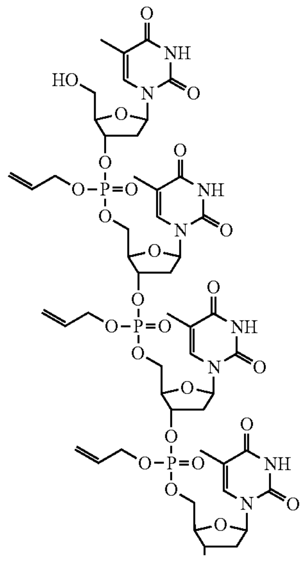

-continued
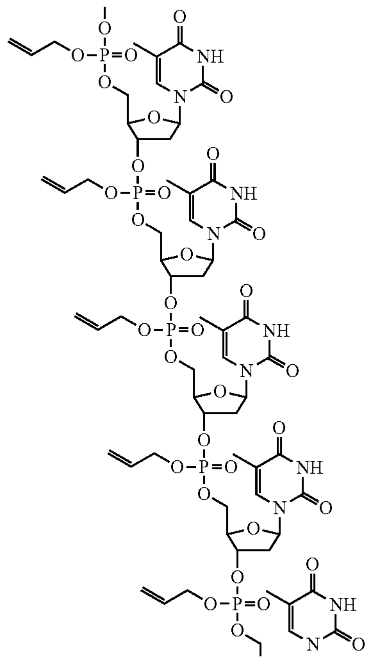
+
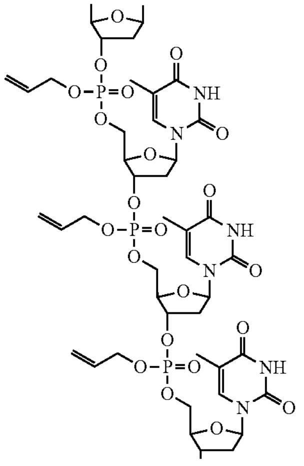
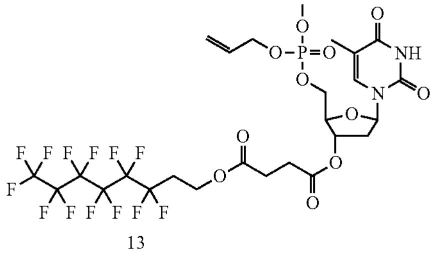
13

-continued
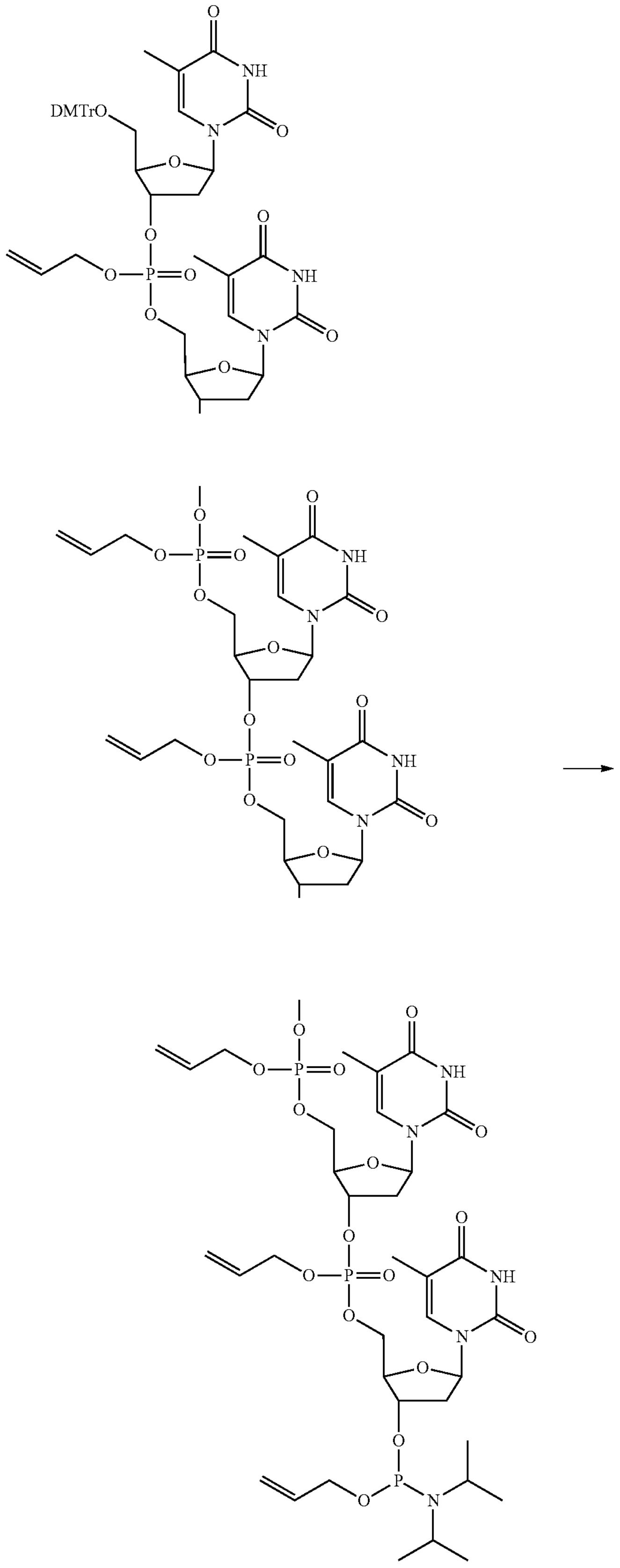
9

-continued
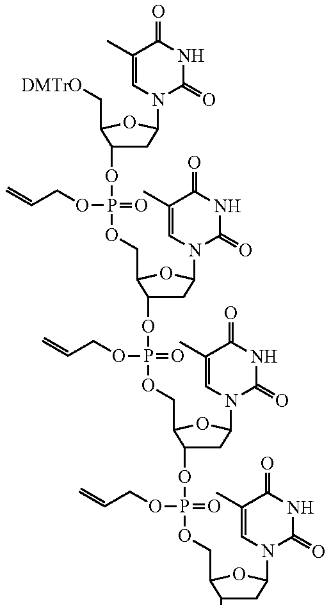
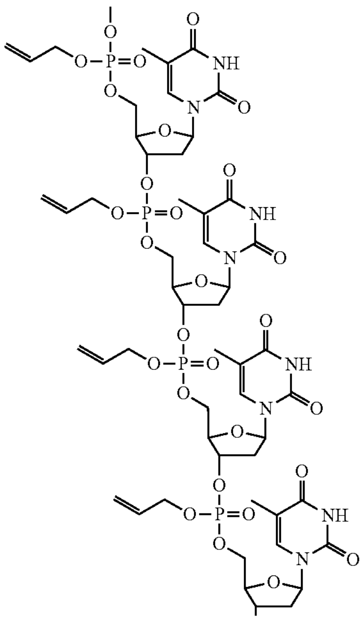

-continued
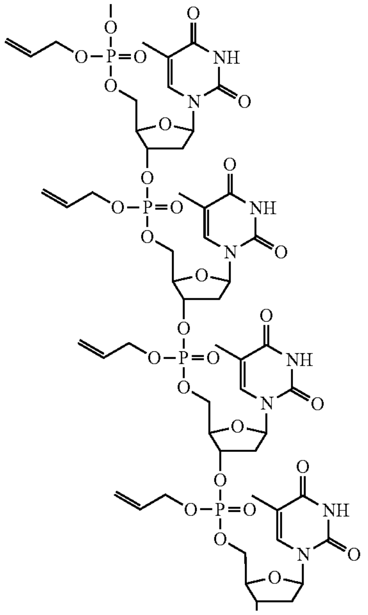
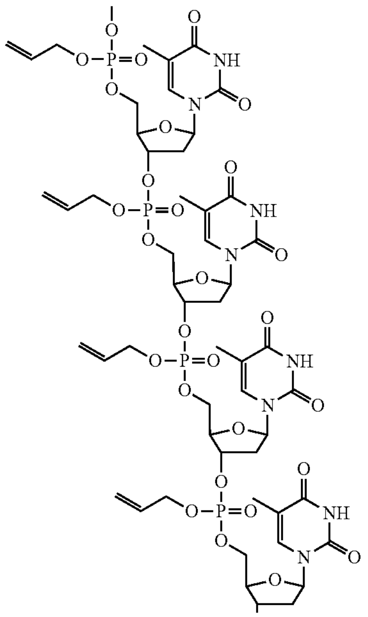

-continued

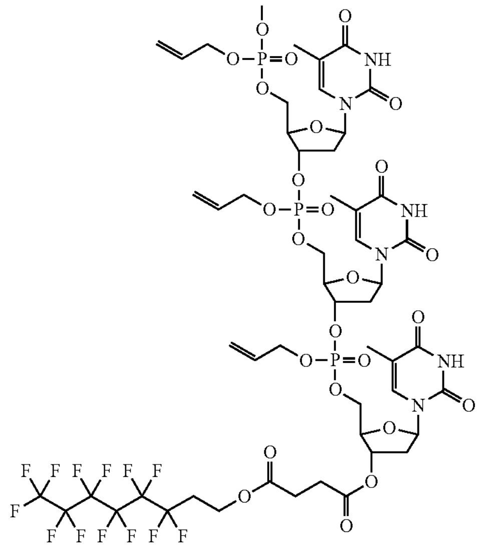

14

Compound 9 (230 mg, 0.093 mmol) and compound 13 (300 mg, 0.062 mmol) were mixed together and then vacuum-dried, and the pressure was set to normal pressure by filling there with argon gas flow. Thereto, molecular sieves 3 A (500 mg) and then dichloromethane:acetonitrile=1:1 solution (5 mL) were added, and the resultant was stirred for 2 hours. Thereto, 5-ethyl-1H-tetrazole (32 mg, 0.25 mmol) was added, and the resultant was stirred at room temperature for 30 minutes. After checking the progression of reaction, 31 wt % 2-butanone peroxide/2,2,4-trimethyl-1,3-pentane diisobutyrate solution (0.060 mL, 0.093 mmol) was added, and the reaction was allowed to continue. After 30 minutes, the reaction mixture was filtered through a Celite, concentrated to reach a solution volume of 5 mL, and then subjected to silica gel column chromatography. A fraction eluted with dichloromethane:methanol=6:1 was collected to afford 82 mg (0.011 mmol) of 5'-protected phosphate-protected T nonadecamer 14 with 3'-bonding fluorous anchor, as the target, at a yield of 18%.

Step 11: Deprotection of 5'-Protected Nucleotide Nonadecamer with 3'-Bonding Fluorous Anchor

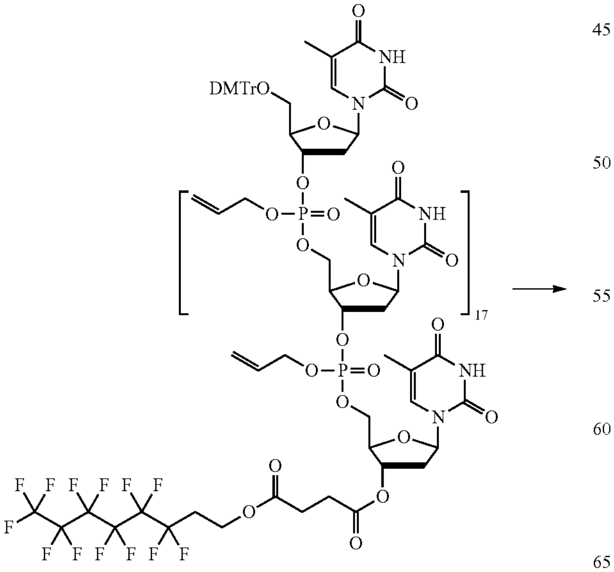

14

-continued

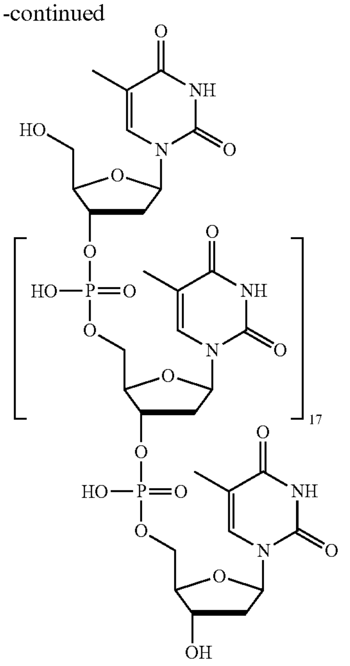

15

Figure 3:
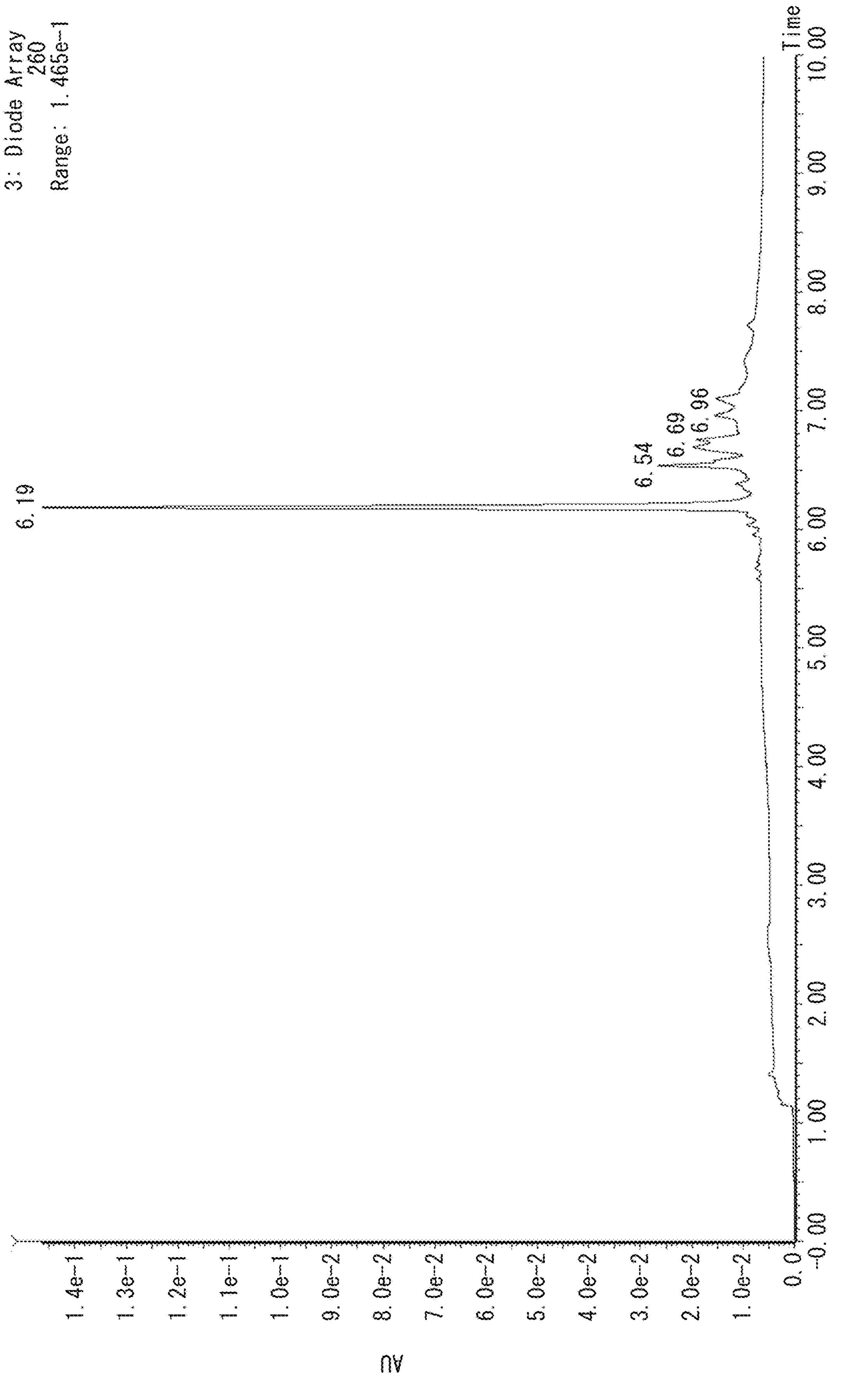
FIG. 3 shows a UPLC spectrum for compound 15 obtained in Examples of the present invention.
Figure 4:
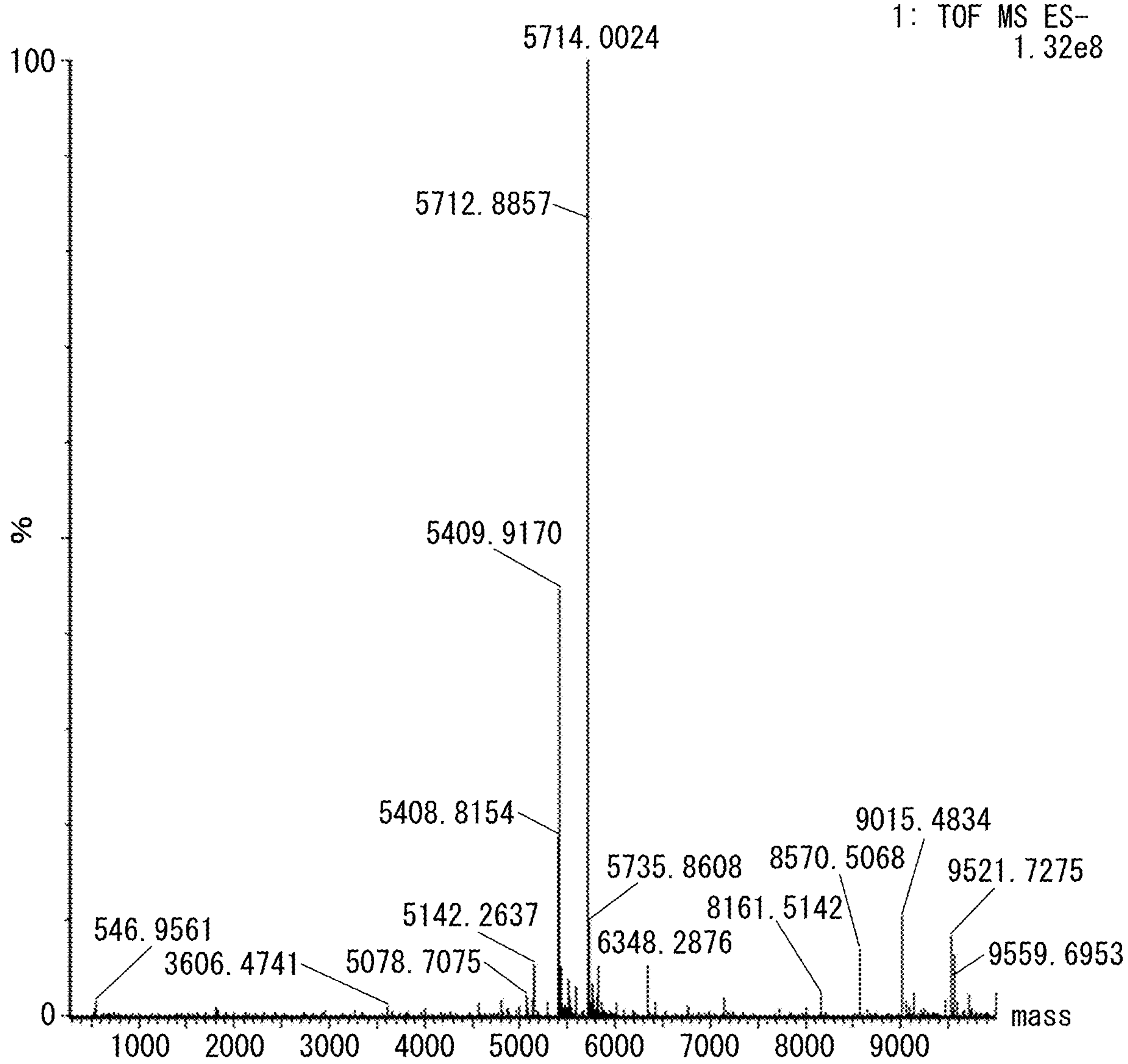
FIG. 4 shows an ESI-TOF mass spectrum for compound 15 obtained in Examples of the present invention.

Compound 14 was dissolved in methanol:concentrated ammonia water=1:1 solution of 1% Q-mercaptoethanol, and the resultant was stirred at 50° C. for 12 hours. The reaction product was subjected to removal of the dimethoxytrityl group and purification with a commercially available purification kit to confirm that compound 15, as the target, could be obtained. A molecular ion peak indicative of the T nonadecamer, $[M-H]^-$ 5714.00 (molecular formula: $C_{190}H_{247}N_{38}O_{131}P_{18}^-$, calc.: 5713.91), was found through observation to confirm the resultant to be the target nonadecamer. FIGS. 3 and 4 show the UPLC spectrum and the ESI-TOF mass spectrum, respectively, for T nonadecamer 15 obtained.

(Example 4) Synthesis of Undecamer Using Nucleoside with Fluorous-Protected Base Moiety

Step 12: Synthesis of 5',3'-Protected Nucleotide Tetramer Containing Nucleoside with Fluorous-Protected Base Moiety by Condensation Between 3'-Phosphoramidite of 5'-Protected Nucleoside with Fluorous-Protected Base Moiety and 5'-Unprotected 3'-Protected Nucleotide Trimer

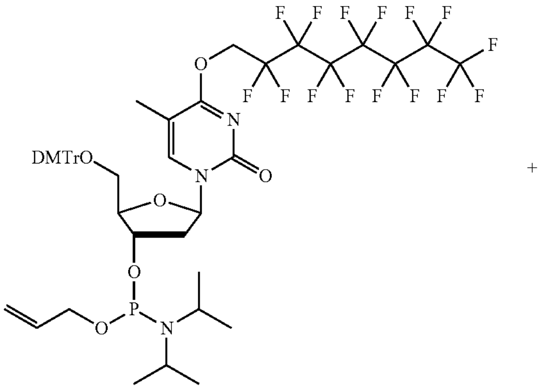

6

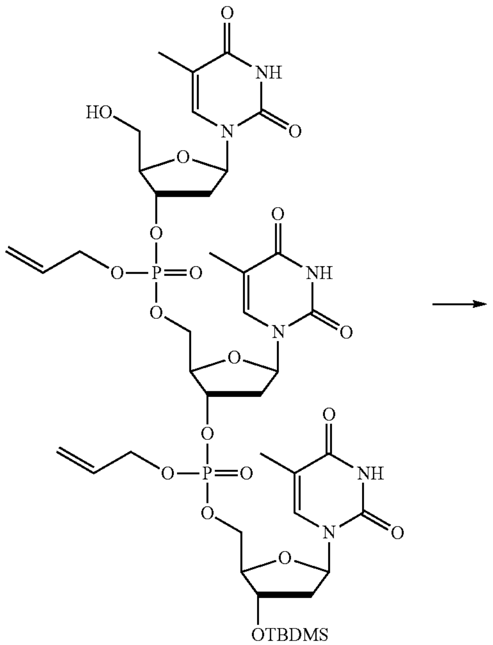

16

-continued

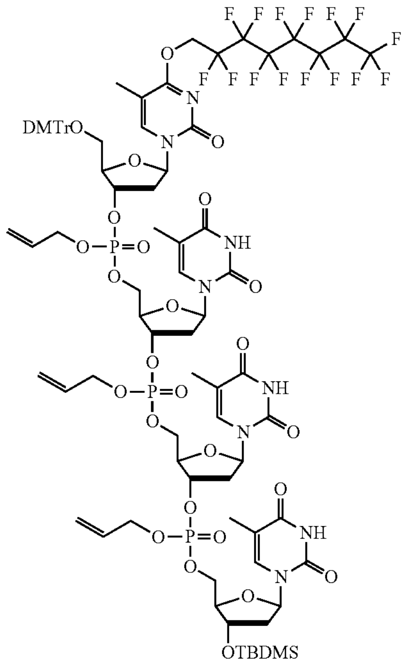

17

Compound 16 (1.05 g, 1.00 mmol) and compound 4 (1.34 g, 1.20 mmol) were dissolved in a dichloromethane-acetonitrile 1:1 mixture (16 mL), to which 1H-tetrazole (350 mg, 5.00 mmol) was further added, and the resultant was stirred. After 15 minutes, 31 wt % 2-butanone peroxide (966 μL, 1.50 mmol) was added dropwise, and the resultant was stirred for 15 minutes. After confirming that the raw materials had almost completely disappeared by TLC (100% ethyl acetate), liquid separation and washing were performed, and the resultant was then subjected to column chromatography to afford 5',3'-protected nucleotide tetramer 17 (1.93 g, 0.93 mmol, yield: 93%, purity: 97%), as the target. The structure was confirmed by $^{31}P$ NMR and ESI-MS, and the purity was confirmed by UPLC.

Step 13: 3'-Deprotection of 5',3'-Protected Nucleotide Tetramer Containing Nucleoside with Fluorous-Protected Base Moiety

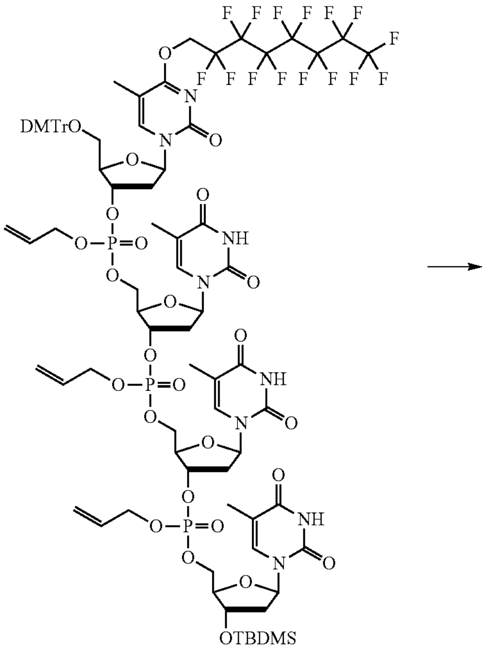

17

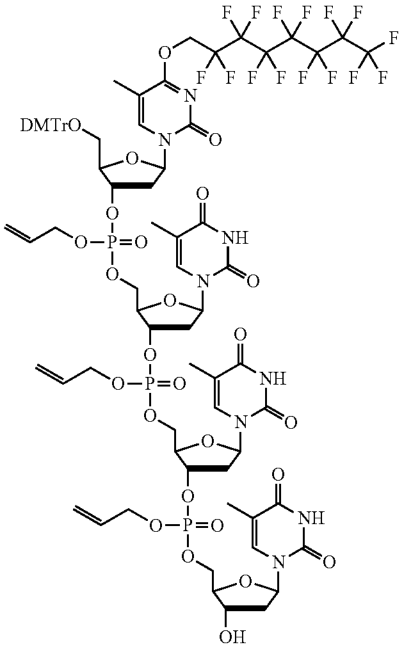

18

Acetic acid (51.4 μL, 0.900 mmol) was added to 5',3'-protected nucleotide tetramer 17 (1.87 g, 0.900 mmol), and the resultant was cooled to 0° C. Thereto, 1.0 M TBAF in THF (1.80 mL, 1.80 mmol) was added dropwise, and the resultant was stirred for 3 hours. After confirming that the raw materials had almost completely disappeared by TLC (ethyl acetate=100%), liquid separation and washing were performed, and the resultant was then subjected to column chromatography to afford 3'-deprotected tetramer 18 (1.35 g, 0.689 mmol, yield: 76.7%, purity: 93%), as the target. The structure was confirmed by $^{31}P$ NMR and ESI-MS, and the purity was confirmed by UPLC.

Step 14: 3'-Phosphitylation of 5'-Protected Nucleotide Tetramer Containing Nucleoside with Fluorous-Protected Base Moiety

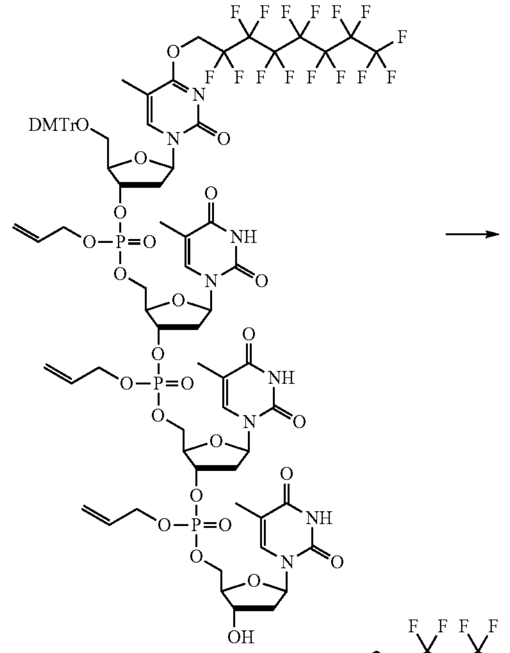

18

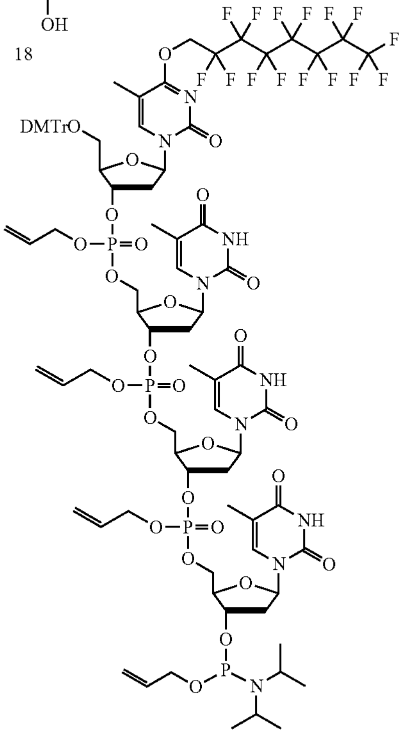

19

Compound 18 (1.27 g, 0.65 mmol) was dissolved in a dichloromethane-acetonitrile 1:1 mixture (16 mL), to which 1H-tetrazole (59.0 mg, 0.845 mmol) and N-methylimidazole (21.0 μL, 0.260 mmol) were further added, and the temperature was set to 0° C. After 15 minutes, allyl N,N,N',N'-tetraisopropylphosphoramidite (469 μL, 1.63 mmol) was added dropwise. After 4 days, it was confirmed that the raw materials had almost completely disappeared by TLC (hexane:ethyl acetate=2:1), and the reaction mixture was directly subjected to column chromatography to afford tetrameric phosphoramidite form 19 (0.873 g, 0.40 mmol, yield: 62.6%, purity: 98.3%), as the target. The structure was confirmed by ESI-MS, and the purity was confirmed by UPLC.

Step 15: Phosphitylation of 5',3'-Protected Nucleotide Heptamer Containing Nucleoside with Fluorous-Protected Base Moiety by Condensation Between 3'-Phosphoramidite of 5'-Protected Nucleotide Tetramer Containing Nucleoside with Fluorous-Protected Base Moiety and 5'-Unprotected 3'-Protected Nucleotide Trimer

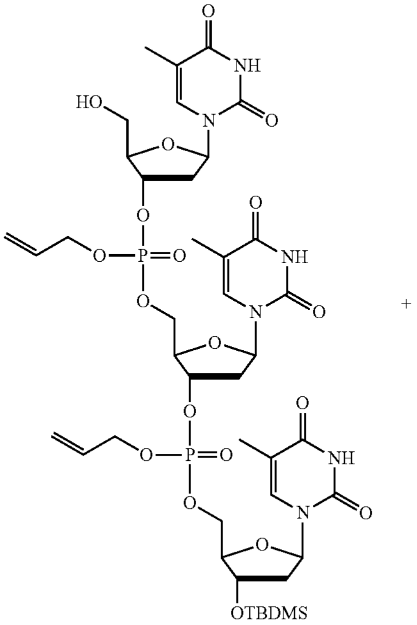

16

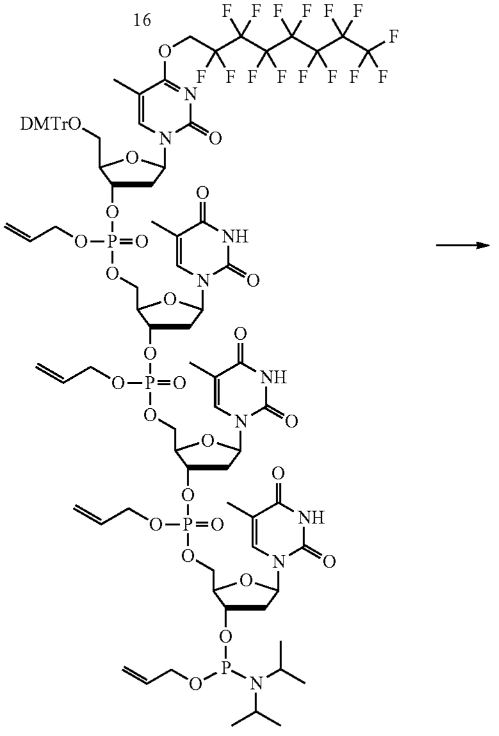

19

-continued

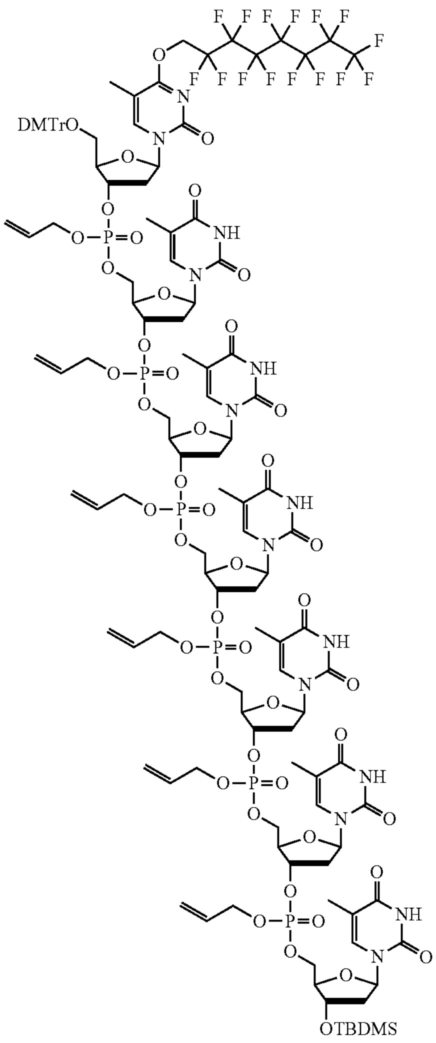

20

Compound 16 (0.537 g, 0.25 mmol) and tetrameric phosphoramidite 19 (0.288 g, 0.275 mmol) were dissolved in a dichloromethane-acetonitrile 1:1 mixture (5 mL), to which 5-ethylthio-1H-tetrazole (70.1 mg, 1.00 mmol) was added, and the resultant was stirred. After 90 minutes, 31 wt % 2-butanone peroxide (241 μL, 0.375 mmol) was added dropwise, and the resultant was stirred for 60 minutes. After confirming that the raw materials had almost completely disappeared by TLC (ethyl acetate:methanol=9:1), liquid separation and washing were performed, and the resultant was then subjected to column chromatography to afford heptamer 20 (0.655 g, 0.211 mmol, yield: 84.3%, purity: 96.7%), as the target. The structure was confirmed by ESI-MS, and the purity was confirmed by UPLC.

Step 16: 5'-Deprotection of 5',3'-Protected Nucleotide Heptamer Containing Nucleoside with Fluorous-Protected Base Moiety

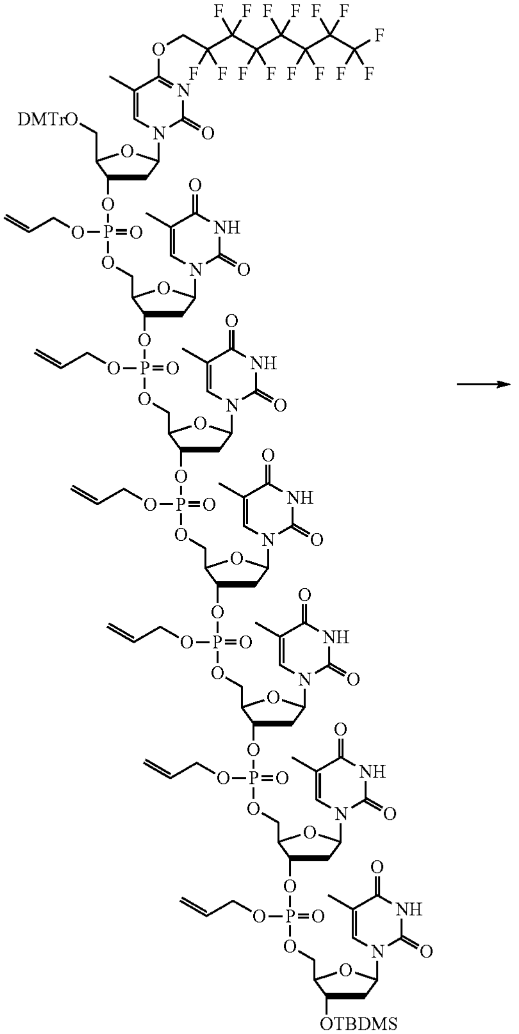

20

-continued

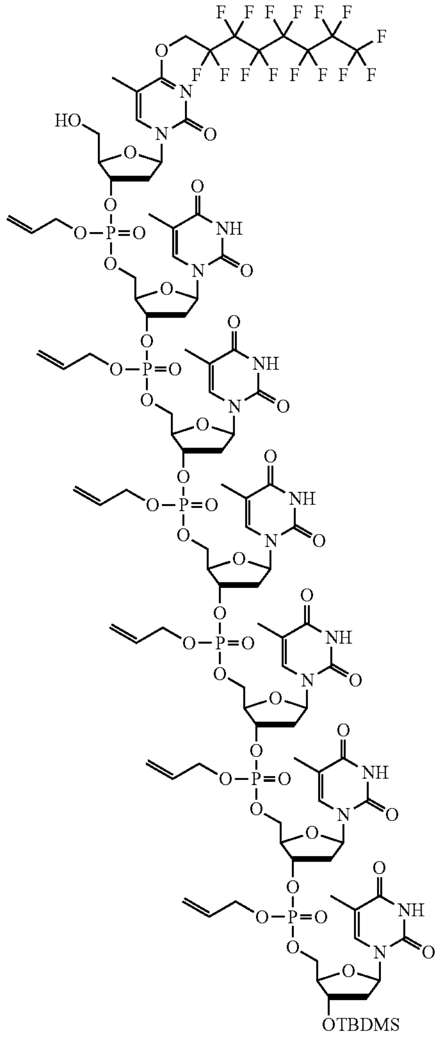

21

Dichloromethane (4 mL) was added to compound 20 (0.655 g, 0.211 mmol), and the resultant was cooled to 0° C. Dichloroacetic acid (0.349 mL, 4.22 mmol) was added dropwise, and the resultant was stirred for 30 minutes. After confirming that the raw materials had almost completely disappeared by TLC (ethyl acetate:methanol=9:1), the reaction solution was subjected to column chromatography to afford 5'-unprotected heptamer 21 (0.468 g, 0.689 mmol, yield: 79.1%, purity: 92.4%), as the target. The purity was confirmed by UPLC.

Step 17: Synthesis of 5',3'-Protected Nucleotide Undecamer Containing Nucleoside with Fluorous-Protected Base Moiety by Condensation Between 3'-Phosphoramidite of 5'-Protected Nucleotide Tetramer Containing Nucleoside with Fluorous-Protected Base Moiety and 5'-Unprotected 3'-Protected Nucleotide Heptamer Containing Nucleoside with Fluorous-Protected Base Moiety

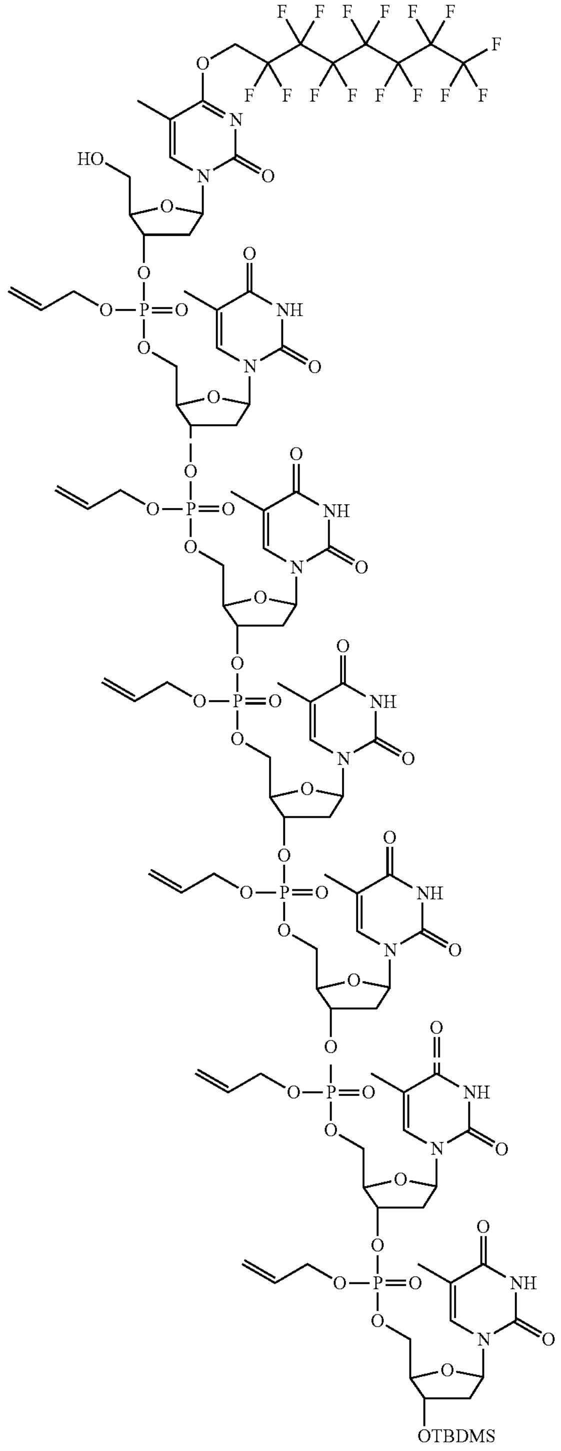

21

+

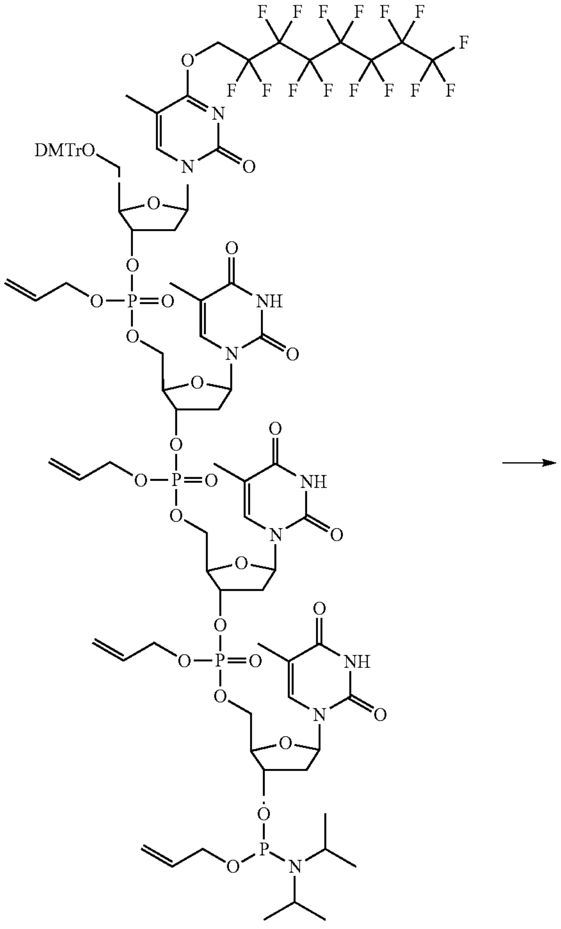

19

-continued
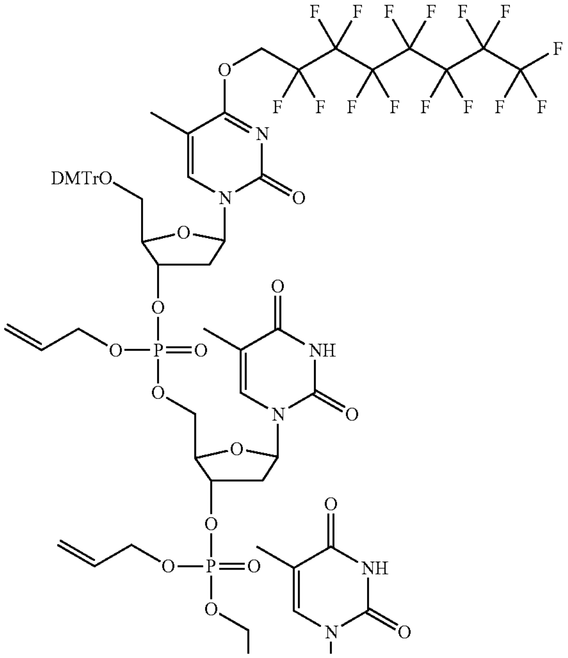
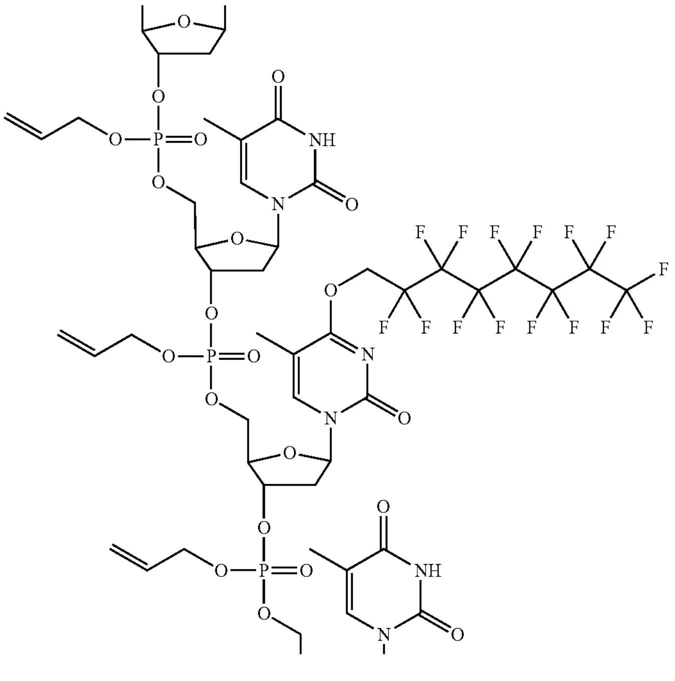

-continued

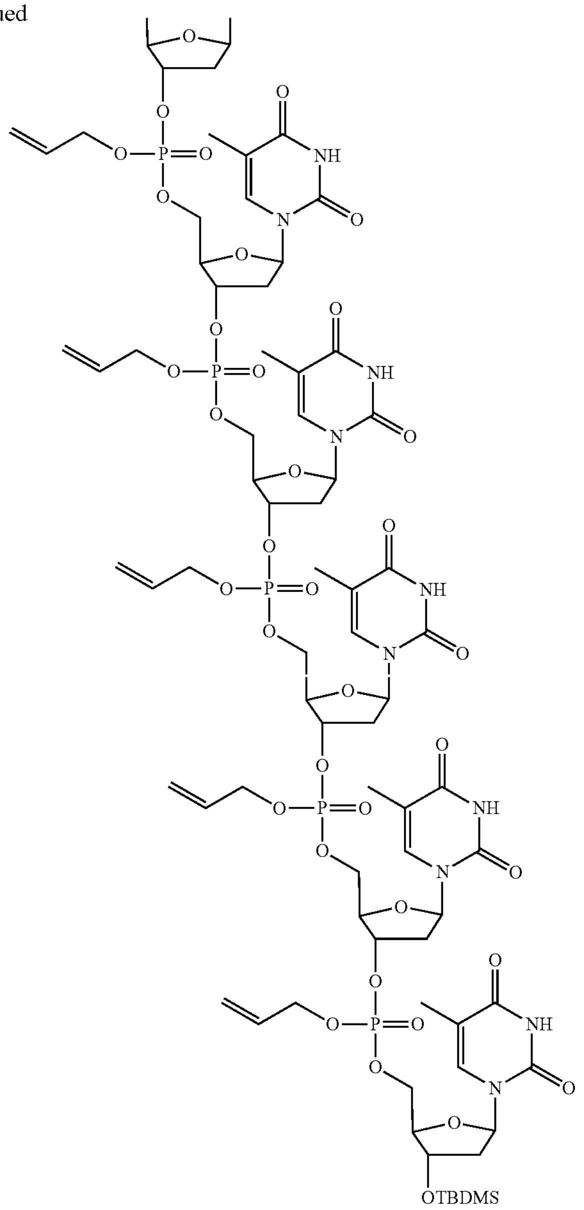

22

Figure 5:
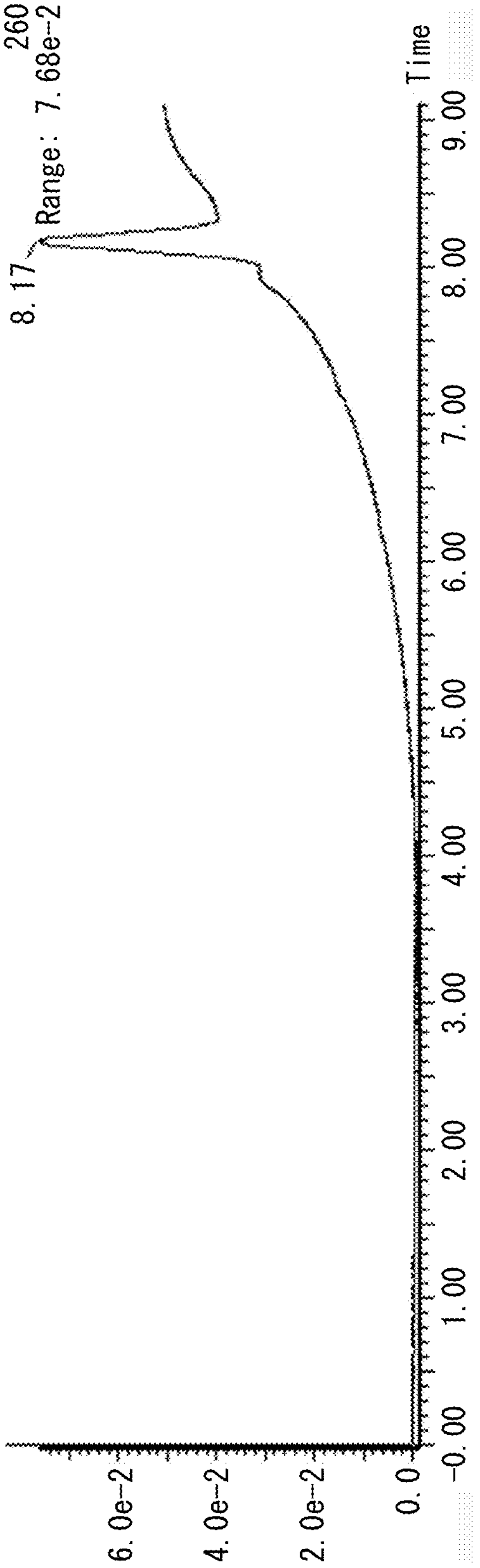
FIG. 5 shows a UPLC spectrum for compound 22 obtained in Examples of the present invention.

In a dichloromethane-acetonitrile 1:1 mixture (2 mL), 5'-unprotected heptamer 21 (0.311 g, 0.100 mmol) and tetrameric phosphoramidite 19 (0.236 g, 0.110 mmol) were dissolved, to which 1H-tetrazole (42.0 mg, 6.00 mmol) and N-methylimidazole (16 μL, 0.200 mmol) were added thereto, and the resultant was stirred. After 90 minutes, 31 wt % 2-butanone peroxide (100 μL, 0.150 mmol) was added dropwise, and the resultant was stirred for 60 minutes. After confirming that the raw materials had almost completely disappeared, liquid separation and washing were performed by TLC (ethyl acetate:methanol=9:1), and the resultant was then subjected to column chromatography to afford 5',3'-protected nucleotide undecamer 22 containing nucleoside with the fluorous-protected base moiety (0.450 g, 0.0920 mmol, yield: 92%, purity: 96.7%), as the target. The purity was confirmed by UPLC. FIG. 5 shows the UPLC spectrum.

A nucleotide undecamer with protecting groups removed therefrom can be obtained by performing deprotection for 5',3'-protected nucleotide undecamer 22 containing nucleoside with the fluorous-protected base moiety with use of a conventionally used method.

Figure 6:
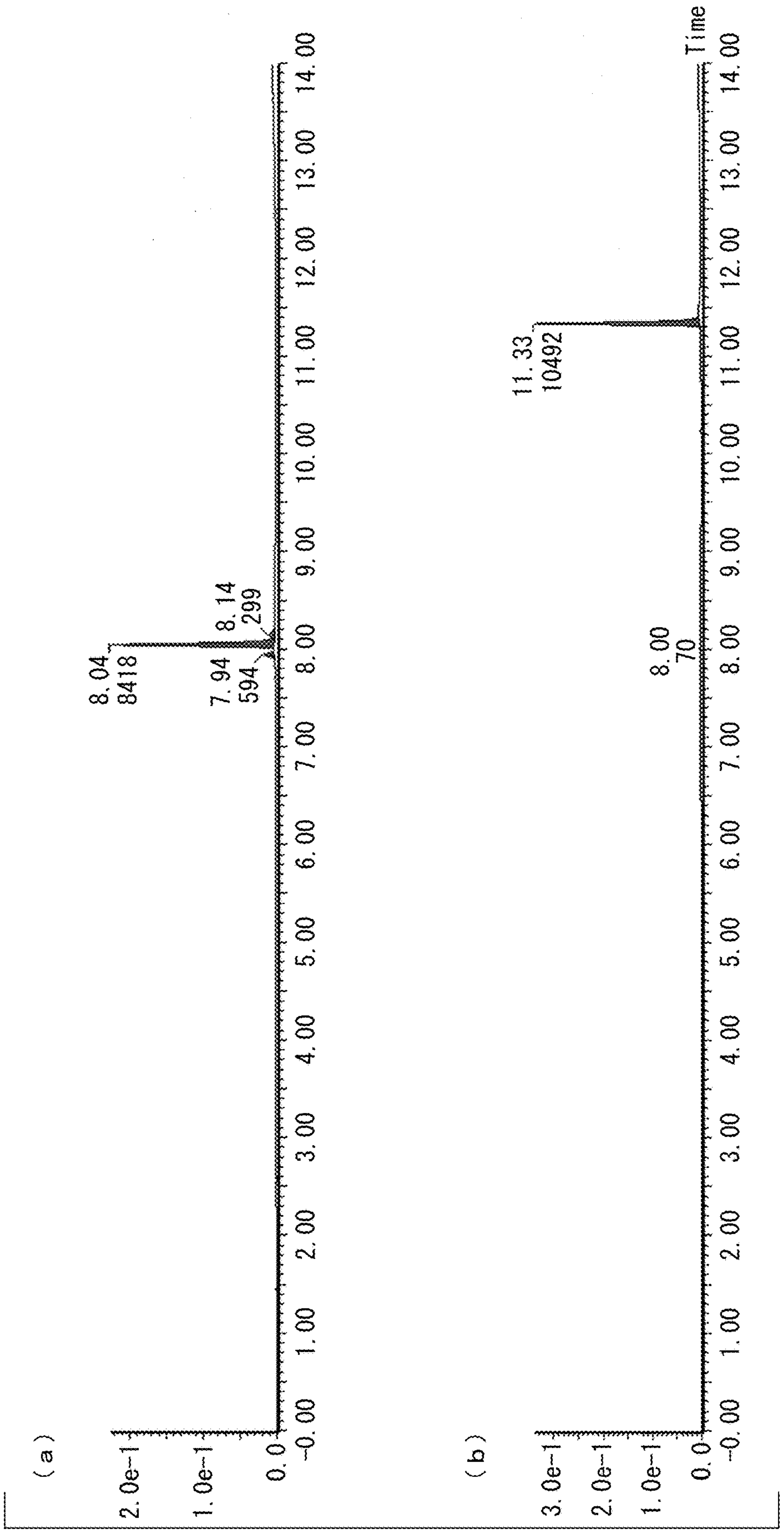
FIG. 6 shows a spectrum for an icosamer synthesized with the synthesis method according to the present invention and a spectrum for an icosamer synthesized with a conventional method.

FIG. 6 shows UPLC spectra for comparison between the post-deprotection purity of a nucleotide icosamer with a $dTA_{19}$ sequence synthesized with a conventional method and the post-deprotection purity of a nucleotide icosamer with a $dTA_{19}$ sequence synthesized with the synthesis method using the fluorous tag according to the present invention. FIG. 6(*a*) is a spectrum for a $dTA_{19}$ icosamer synthesized with a conventional method, and FIG. 6(*b*) is a spectrum for the $dTA_{19}$ icosamer having the fluorous tag according to the present invention on the base moiety of 5'-end T. It can be understood that an icosamer of higher purity than the icosamer synthesized with a conventional method was successfully provided by performing deprotection so as to allow the fluorous tag to remain and then purification. It was demonstrated that the high lipid solubility of the fluorous tag largely changes retention time in separation/purification, thereby allowing simpler isolation/purification than in the conventional method.

The multi-fluorous blockmer of the above embodiments according to the present invention can be synthesized by introducing a fluorous anchor with use of a commercially available fluorocarbon derivative as it is. The number of fluorine atoms in the fluorous anchor can be readily changed according to the purpose. Hence, a target product can be obtained more readily with lower cost than in the case with introduction of a fluorous tag into nucleoside by using any conventional method, which requires complicated steps for obtaining an intended fluorous tag.

In introduction of a fluorous tag into nucleoside by using any conventional method, the number of molecules of a fluorous tag to be introduced is limited because of the problems as described above, and thus the conventional methods do not have high versatility. By contrast, the synthesis of the multi-fluorous blockmer of the above embodiments according to the present invention can change solubility of intermediates in oligonucleotide synthesis and reduce burdens of purification through adjustment of the number of molecules of the fluorous anchor to be introduced. Thereby, a more versatile synthesis method can be achieved. According to the length or sequence of the blockmer or oligonucleotide to be synthesized, the fluorous tag can be introduced to the base moiety of nucleoside or to a protecting group at the 3'-end of nucleoside.

The oligonucleotide synthesis method using the multi-fluorous blockmer of the above embodiments according to the present invention can form an oxidized/sulfidized pentavalent-phosphate-bonding moiety as early as at the stage of a blockmer. Accordingly, even in the case that only some of the phosphate bonds in oligonucleotide are to be made into oxidation/sulfurization states differing from those of the other phosphate bonds, a target oligonucleotide containing modified phosphate-bonding moieties can be synthesized in a simpler manner without changing the procedure of oligonucleotide synthesis.

Conventionally used blockmers with a fluorous tag introduced thereinto are influenced by the physical properties of the fluorous tag, and thus require a complicated purification method in chain elongation in oligonucleotide synthesis. By contrast, the method for synthesizing the multi-fluorous blockmer and oligonucleotide synthesis method using the multi-fluorous blockmer of above embodiments according to the present invention have a large degree of freedom in selecting a purification method according to the chain length, allowing selection from silica gel filtration, purification by affinity chromatography, separation with fluorous solvent-hydrocarbon organic solvent, and so on. Thus, a target oligonucleotide can be obtained with simpler purification than in oligonucleotide synthesis methods using a fluorous tag according to any conventional method.

With the oligonucleotide synthesis method using the multi-fluorous blockmer of the above embodiments according to the present invention, the number of necessary steps can be reduced in synthesizing an N-meric oligonucleotide as compared with methods of elongating base by base with any conventionally used liquid-phase synthesis method. Accordingly, an improved yield of oligonucleotide of intended length can be achieved.

The invention claimed is:

1. A protected nucleoside for oligonucleotide synthesis represented by formula (I):

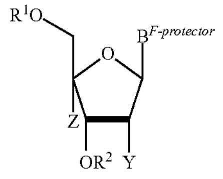

(I)

wherein B is a natural nucleoside base; $R^1$ and $R^2$ are each independently H or a protecting group that can be removed for deprotection under acidic, basic, or neutral conditions; F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 4 to 20; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y.

2. A 5'-end-protected nucleoside phosphoramidite for oligonucleotide synthesis represented by formula (II):

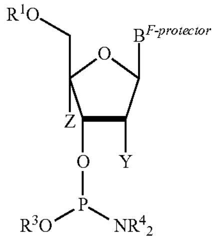

(II)

wherein B is a natural nucleoside base; $R^1$ is a protecting group that can be removed for deprotection under acidic, basic, or neutral conditions; $R^3$ is a protecting group for a phosphate group, or is taken together with one of the groups of $R^4$ bonding to the nitrogen atom bonding to the phosphorus atom to form a ring; $R^4$ is a substituted or unsubstituted aliphatic group or a substituted or unsubstituted aromatic group; F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; Y is H, OH, a halogen, $OCH_3$, methoxyethyl, CN, $CF_3$, or a hydroxy group protected with an acyl protecting group, an ether protecting group, or a silyl protecting group; and Z is H, an alkyl, an O-alkyl, an N-alkyl, or a halogen, or forms a Z—Y bond with Y.

3. A fluorous blockmer phosphoramidite for oligonucleotide synthesis represented by formula (III):

(III)

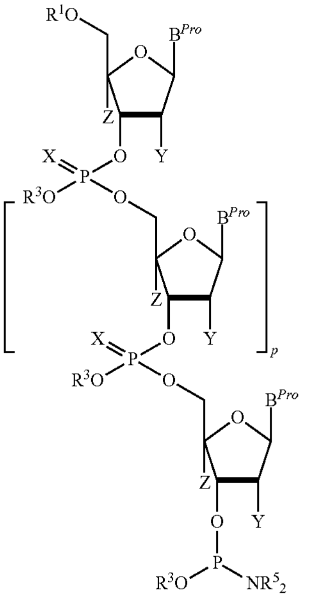

wherein B is a natural nucleoside base; $R^1$ is a protecting group that can be removed for deprotection under acidic, basic, or neutral conditions; $R^3$ is a protecting group for a phosphate group, or is taken together with one of the groups of $R^5$ bonding to the nitrogen atom bonding to the phosphorus atom forming the phosphoramidite moiety to form a ring; $R^5$ is a substituted or unsubstituted aliphatic group or a substituted or unsubstituted aromatic group; Pro is a protecting group for a nucleoside base, or F-protector, wherein F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; X is O or S; p is an integer of 0 to 27; Y is H, OH, a halogen, $OCH_3$, methoxyethyl, CN, $CF_3$, or a hydroxy group protected with an acyl protecting group, an ether protecting group, or a silyl protecting group; Z is H, an alkyl, an O-alkyl, an N-alkyl, or a halogen, or forms a Z—Y bond with Y; and the fluorous blockmer phosphoramidite has at least one group of F-protector at any of the groups of Pro, $R^1$, and $R^3$.

4. A multi-fluorous blockmer for oligonucleotide synthesis represented by formula (IV):

(IV)

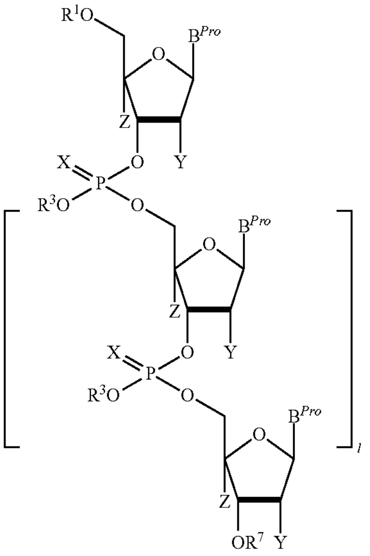

wherein B is a natural nucleoside base; $R^1$ is a protecting group that can be removed for deprotection under acidic, basic, or neutral conditions; $R^3$ is a protecting group for a phosphate group; Pro is a protecting group for a nucleoside base, or F-protector, wherein F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; X is O or S; 1 is an integer of 0 to 58; $R^7$ is $(C{=}O)(CH_2)_2(C{=}O)(CH_2)_n(CF_2)_mCF_3$ or a silyl protecting group, wherein n is 1 or 2 and m is an integer of 1 to 20; Y is H, OH, a halogen, $OCH_3$, methoxyethyl, CN, $CF_3$, or a hydroxy group protected with an acyl protecting group, an ether protecting group, or a silyl protecting group; Z is H, an alkyl, an O-alkyl, an N-alkyl, or a halogen, or forms a Z—Y bond with Y; and the multi-fluorous blockmer has at least one group of F-protector at any of the groups of Pro, $R^1$, and $R^3$.

5. A method for synthesizing the multi-fluorous blockmer for oligonucleotide synthesis represented by formula (IV) according to claim 4, the method comprising a step of performing coupling reaction between the fluorous blockmer phosphoramidite represented by formula (III) according to claim 3 or a 5'-end-protected nucleoside H-phosphonate represented by formula (II') and a nucleoside represented by formula (V) with a fluorous anchor bonding to the 3'-end of the nucleoside:

(II')

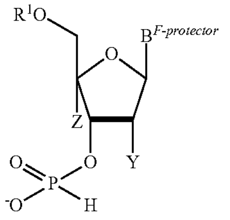

-continued (V)

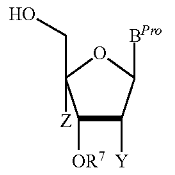

wherein B is a natural nucleoside base; $R^1$ is a protecting group that can be removed for deprotection under acidic, basic, or neutral conditions; F-protector is $O(CH_2)_n(CF_2)_mCF_3$ when the protected moiety of nucleoside base B is O, and is $NH(C{=}O)(CH_2)_n(CF_2)_mCF_3$ when the protected moiety of nucleoside base B is N, wherein n is 1 or 2 and m is an integer of 1 to 20; Y is H, OH, a halogen, $OCH_3$, methoxyethyl, CN, $CF_3$, or a hydroxy group protected with an acyl protecting group, an ether protecting group, or a silyl protecting group; Z is H, an alkyl, an O-alkyl, an N-alkyl, or a halogen, or forms a Z—Y bond with Y; $R^7$ is $(C{=}O)(CH_2)_2(C{=}O)(CH_2)_n(CF_2)_mCF_3$ or a silyl protecting group, wherein n is 1 or 2 and m is an integer of 1 to 20.

6. The protected nucleoside according to claim 1,
- wherein the protecting group that can be removed for deprotection under acidic conditions is a substituted or unsubstituted trityl group, a pixyl group, or a substituted or unsubstituted tetrahydropyranyl (THP) group,
- wherein the protecting group that can be removed for deprotection under basic conditions is an Fmoc group or a pivaloyl group,
- wherein the protecting group that can be removed for deprotection under neutral conditions is a trimethylsilyl group, a triethylsilyl group, a t-butyldimethylsilyl group, a t-butyldiphenylsilyl group, or a triphenylsilyl group,
- wherein the acyl protecting group is an acyl group, an acetyl group, a benzoyl group, or a pivaloyl group,
- wherein the ether protecting group is a pixyl group, or a substituted or unsubstituted tetrahydropyranyl (THP) group, and
- wherein the silyl protecting group is a trimethylsilyl group, a triethylsilyl group, a t-butyldimethylsilyl group, a t-butyldiphenylsilyl group, or a triphenylsilyl group.

7. The 5'-end-protected nucleoside phosphoramidite according to claim 2,
- wherein the protecting group that can be removed for deprotection under acidic conditions is a substituted or unsubstituted trityl group, a pixyl group, or a substituted or unsubstituted tetrahydropyranyl (THP) group,
- wherein the protecting group that can be removed for deprotection under basic conditions is an Fmoc group or a pivaloyl group,
- wherein the protecting group that can be removed for deprotection under neutral conditions is a trimethylsilyl group, a triethylsilyl group, a t-butyldimethylsilyl group, a t-butyldiphenylsilyl group, or a triphenylsilyl group, and
- wherein the protecting group for a phosphate group is $—CH_2CH_2CN$, a fluorine-containing protecting group, $—CH_2CH{=}CH_2$, $—OCH_3$, a 2-chlorophenyl group, or a phenyl group.

8. The fluorous blockmer phosphoramidite according to claim 3,
- wherein the protecting group that can be removed for deprotection under acidic conditions is a substituted or unsubstituted trityl group, a pixyl group, or a substituted or unsubstituted tetrahydropyranyl (THP) group,
- wherein the protecting group that can be removed for deprotection under basic conditions is an Fmoc group or a pivaloyl group,
- wherein the protecting group that can be removed for deprotection under neutral conditions is a trimethylsilyl group, a triethylsilyl group, a t-butyldimethylsilyl group, a t-butyldiphenylsilyl group, or a triphenylsilyl group,
- wherein the protecting group to protect a nucleoside base is an acyl group, a benzoyl group, or an allyloxycarbonyl group,
- wherein the acyl protecting group is an acyl group, an acetyl group, a benzoyl group, or a pivaloyl group,
- wherein the ether protecting group is a pixyl group, or a substituted or unsubstituted tetrahydropyranyl (THP) group, and
- wherein the silyl protecting group is a trimethylsilyl group, a triethylsilyl group, a t-butyldimethylsilyl group, a t-butyldiphenylsilyl group, or a triphenylsilyl group, and
- wherein the protecting group for a phosphate group is $—CH_2CH_2CN$, a fluorine-containing protecting group, $—CH_2CH{=}CH_2$, $—OCH_3$, a 2-chlorophenyl group, or a phenyl group,
- wherein the fluorine-containing protecting group is $O(CH_2)_n(CF_2)_mCF_3$ wherein n is 1 or 2 and m is an integer of 1 to 20.

9. The multi-fluorous blockmer according to claim 4,
- wherein the protecting group that can be removed for deprotection under acidic conditions is a substituted or unsubstituted trityl group, a pixyl group, or a substituted or unsubstituted tetrahydropyranyl (THP) group,
- wherein the protecting group that can be removed for deprotection under basic conditions is an Fmoc group or a pivaloyl group,
- wherein the protecting group that can be removed for deprotection under neutral conditions is a trimethylsilyl group, a triethylsilyl group, a t-butyldimethylsilyl group, a t-butyldiphenylsilyl group, or a triphenylsilyl group,
- wherein the protecting group to protect a nucleoside base is an acyl group, a benzoyl group, or an allyloxycarbonyl group,
- wherein the acyl protecting group is an acyl group, an acetyl group, a benzoyl group, or a pivaloyl group,
- wherein the ether protecting group is a pixyl group, or a substituted or unsubstituted tetrahydropyranyl (THP) group,
- wherein the silyl protecting group is a trimethylsilyl group, a triethylsilyl group, a t-butyldimethylsilyl group, a t-butyldiphenylsilyl group, or a triphenylsilyl group, and
- wherein the protecting group for a phosphate group is $—CH_2CH_2CN$, a fluorine-containing protecting group, $—CH_2CH{=}CH_2$, $—OCH_3$, a 2-chlorophenyl group, or a phenyl group,
- wherein the fluorine-containing protecting group is $O(CH_2)_n(CF_2)_mCF_3$ wherein n is 1 or 2 and m is an integer of 1 to 20.

10. The method for synthesizing the multi-fluorous blockmer according to claim 5,
- wherein the protecting group that can be removed for deprotection under acidic conditions is a substituted or unsubstituted trityl group, a pixyl group, or a substituted or unsubstituted tetrahydropyranyl (THP) group, wherein the protecting group that can be removed for deprotection under basic conditions is an Fmoc group or a pivaloyl group, wherein the protecting group that can be removed for deprotection under neutral conditions is a trimethylsilyl group, a triethylsilyl group, a t-butyldimethylsilyl group, a t-butyldiphenylsilyl group, or a triphenylsilyl group, wherein the acyl protecting group is an acyl group, an acetyl group, a benzoyl group, or a pivaloyl group, wherein the ether protecting group is a pixyl group, or a substituted or unsubstituted tetrahydropyranyl (THP) group, and wherein the silyl protecting group is a trimethylsilyl group, a triethylsilyl group, a t-butyldimethylsilyl group, a t-butyldiphenylsilyl group, or a triphenylsilyl group.

* * * * *